United States Patent
Scheidt-Puga

(10) Patent No.: US 11,898,175 B2
(45) Date of Patent: Feb. 13, 2024

(54) TREATMENT OF ABNORMAL BONE CONDITIONS IN ACID SPHINGOMYELINASE DEFICIENCY PATIENTS

(71) Applicant: Genzyme Corporation, Cambridge, MA (US)

(72) Inventor: Ana Cristina Scheidt-Puga, Paris (FR)

(73) Assignee: Genzyme Corporation, Cambridge, MA (US)

(*) Notice: Subject to any disclaimer, the term of this patent is extended or adjusted under 35 U.S.C. 154(b) by 867 days.

(21) Appl. No.: 16/641,116

(22) PCT Filed: Aug. 22, 2018

(86) PCT No.: PCT/IB2018/056346
§ 371 (c)(1),
(2) Date: Feb. 21, 2020

(87) PCT Pub. No.: WO2019/038685
PCT Pub. Date: Feb. 28, 2019

(65) Prior Publication Data
US 2021/0139868 A1    May 13, 2021

Related U.S. Application Data

(60) Provisional application No. 62/549,732, filed on Aug. 24, 2017.

(30) Foreign Application Priority Data

Dec. 7, 2017   (EP) ..................... 17306720

(51) Int. Cl.
| | | |
|---|---|---|
| C12N 9/16 | (2006.01) | |
| A61P 19/08 | (2006.01) | |
| A61P 3/00 | (2006.01) | |
| A61P 19/10 | (2006.01) | |
| A61K 38/46 | (2006.01) | |
| A61P 19/00 | (2006.01) | |

(52) U.S. Cl.
CPC ............... *C12N 9/16* (2013.01); *A61P 19/08* (2018.01); *C12Y 301/04* (2013.01)

(58) Field of Classification Search
None
See application file for complete search history.

(56) References Cited

U.S. PATENT DOCUMENTS

| | | | |
|---|---|---|---|
| 2010/0137200 A1* | 6/2010 | Clark | ............. A61K 38/30 514/1.1 |
| 2014/0162954 A1 | 6/2014 | Brown et al. | |
| 2015/0071907 A1 | 3/2015 | Crombez et al. | |

FOREIGN PATENT DOCUMENTS

| | | |
|---|---|---|
| WO | 01/31030 A1 | 5/2001 |
| WO | WO 2011/025996 | 3/2011 |
| WO | 2014/197859 A1 | 12/2014 |

OTHER PUBLICATIONS

Wasserstein et al. ("Successful within-patient dose escalation of olipudase alfa in acid sphingomyelinase deficiency", Molecular Genetics and Metabolism, vol. 116, No. 1, May 30, 2015, pp. 88-97).*

American Thoracic Society, "Lung Function Testing—Selection of Reference Values and Interpretative Strategies," Am. Rev. Respir. Dis. (1991) 144: 1202-1218.

Anonymous, "Archive History for Study: NCT02004691", Retrieved from the Internet: URL:https://clinicaltrials.gov/ct2/history/NCT02004691?V _39=View#StudyPageTop (2017) 1-11.

Boot et al., "Plasma chitotriosidase and CCL18 as surrogate markers for granulomatous macrophages in sarcoidosis," Clin Chim Acta (2010) 411(1-2):31-36.

Cassiman et al., "Cause of death in patients with chronic visceral and chronic neurovisceral acid sphingomyelinase deficiency (Niemann-Pick disease type B and B variant): Literature review and report of new cases," Mol Genet Metab. (2016) 118(3):206-213.

Chuang et al., "Lyso-sphingomyelin is elevated in dried blood spots of Niemann-Pick B patients," Mol. Genet. Metab. (2014) 111(2):209-211.

Cleeland, "Pain assessment: the advantages of using pain scales in lysosomal storage diseases" Acta Paediatr Suppl. (2002) 91 (439):43-7.

Crapo et al., "Standardized single breath normal values for carbon monoxide diffusing capacity," Am Rev Respir Dis. (1981) 123(2):185-9.

Deng et al., "Imipramine Protects against Bone Loss by Inhibition of Osteoblast-Derived Microvesicles," Int J of Mol Sci. (2017) 18(5):1013.

Dhami et al., "Analysis of the Lung Pathology and Alveolar Macrophage Function in the Acid Sphingomyelinase—Deficient Mouse Model of Niemann-Pick Disease," Lab Invest. (2001) 81(7):987-99.

Gulbins et al., "Ceramide, membrane rafts and infections," J. Mol. Med. (2004) 82(6):357-363.

Guo et al., "Elevated plasma chitotriosidase activity in various lysosomal storage disorders," J. Inherit. Metab. Dis. (1995) 18(6):717-722.

Jacobson et al., "National Lipid Association Recommendations for Patent-Centered Management of Dyslipidemia: Part 1—Full Report," J. Clin. Lipidol. (2015) 9(2):129-169.

Jama, "Osteoporosis prevention diagnosis and therapy," Consensus Conference (2001) 285(6):785-795.

(Continued)

*Primary Examiner* — Suzanne M Noakes
*Assistant Examiner* — Jae W Lee
(74) *Attorney, Agent, or Firm* — Steptoe LLP; Z. Ying Li; Mauricio Alvarez

(57) ABSTRACT

The invention provides methods of using a human acid sphingomyelinase (e.g., olipudase alfa) in treating an abnormal bone condition in acid sphingomyelinase deficiency patients such as low bone density, high bone marrow burden, and other skeletal abnormalities presented in acid sphingomyelinase deficiency patients.

11 Claims, 4 Drawing Sheets

Specification includes a Sequence Listing.

(56) References Cited

OTHER PUBLICATIONS

Kozawa et al., "Sphingomyelinase amplifies BMP-4-induced osteocalcin synthesis in osteoblasts: role of ceramide," Cell Sign. (2002) 14(12):999-1004.
Maas et al., "Recommendations for the assessment and monitoring of skeletal manifestations in children with Gaucher disease," Skeletal Radiol. (2008) 37(3):185-188.
Maas et al., "Quantification of bone involvement in Gaucher disease: MR imaging bone marrow burden score as an alternative to Dixon quantitative chemical shift MR imaging—initial experience," Radiology (2003) 229(2):554-61.
MacIntyre et al., "Standardisation of the single-breath determination of carbon monoxide uptake in the lung" Eur. Respir. J. (2005) 26(4):720-735.
McGovern et al., "Disease manifestations and burden of illness in patients with acid sphingomyelinase deficiency (ASMD)," Orph J of Rare Dis. (2017) 12(1): 41.
McGovern et al., "Skeletal manifestations in Niemann-Pick disease due to acid sphingomyelinase deficiency," Mol Gen and Metab. (2008) 93(2): S31.
McGovern et al., "Morbidity and mortality in type B Niemann-Pick disease," Genet Med. (2013) 15(8):618-23.
McGovern et al., "Natural history of Type A Niemann-Pick disease possible endpoints for therapeutic trials," Neurology (2006) 66(2):228-32.
McGovern et al., "A Prospective, Cross-sectional Survey Study of the Natural History of Niemann-Pick B Disease," Ped. (2008) 122(2):e341-49.
McGovern et al., "Novel first-dose adverse drug reactions during a phase I trial of olipudase alfa (recombinant human acid sphingomyelinase) in adults with Niemann-Pick disease type B (acid sphingomyelinase deficiency)," Gen in Med. (2016) 18(1):34-40.
Mendoza et al., "The rapid assessment of fatigue severity in cancer patients: use of the Brief Fatigue Inventory," Cancer (1999) 85(5):1186-96.
Miranda et al., "Infusion of recombinant human acid sphingomyelinase into niemann-pick disease mice leads to visceral, but not neurological, correction of the pathophysiology," FASEB J. (2000) 14(13):1988-95.
Pastores et al., "Therapeutic goals in the treatment of Gaucher disease," Semin Hematol (2004) 41 (Supple 5):4-14.
Robertson et al., "Semiquantitative assessment of skeletal response to enzyme replacement therapy for Gaucher's disease using the bone marrow burden score," AJR Am J Roentgenol. (2007) 188(6):1521-28.
Roth et al., "Potent and Selective Inhibition of Acid Sphingomyelinase by Bisphosphonates," Angewandte Chemie International Edition (2009) 48(41):7560-63.
Schuchman et al., "Types A and B Niemann-Pick disease," Mol Genet Metab. (2017) 120(1-2):27-33.
Spiegel et al., "Signal transduction through lipid second messengers," Curr. Opin. Cell Biol. (1996) 8(2):159-167.
Tyagi et al., "Chemical modification and chemical cross-linking for protein/enzyme stabilization" (1998) Biochemistry (Mosc). 63(3):334-44.
Varni et al., "The PedsQL Multidimensional Fatigue Scale in pediatric rheumatology: reliability and validity," J Rheumatol. (2004) 31(12):2494-500.
Varni et al., "PedsQL 4.0: reliability and validity of the Pediatric Quality of Life Inventory version 4.0 generic core scales in healthy and patient populations," Med Care. (2001) 39(8):800-12.
Wasserstein et al., "The Natural History of Type B Niemann-Pick disease: Results From a 10-year Longitudinal Study," Pediatrics (2004) 114(6):e672-7.
Wasserstein et al., "Successful within-patient dose escalation of olipudase alfa in acid sphingomyelinase deficiency," Mol Gen and Metab. (2015) 116(1-2): 88-97.
Wasserstein et al., "Acid sphingomyelinase deficiency: prevalence and characterization of an intermediate phenotype of Niemann-Pick disease," J Pediatr. (2006) 149(4):554-9.
Wasserstein et al., "Olipudase alfa for treatment of acid sphingomyelinase deficiency (ASMD): safety and efficacy in adults treated for 30 months," J of Inh Metab Dis. (2018) 41(5): 829-38.
Wasserstein et al., "Growth restriction in children with type B Niemann-Pick disease," J Pediatr. (2003) 142(4):424-8.
Wasserstein et al., "Skeletal manifestations in pediatric and adult patients with Niemann Pick disease type B," J of Inh Metab Dis. (2013) 36(1): 123-27.
Wenstrup et al., "Effect of enzyme replacement therapy with imiglucerase on BMD in type 1 Gaucher disease," J Bone Miner Res. (2007) 22(1):119-26.
Yakube et al. "Amino acids, peptides, proteins," M.-M: Mir, (1985) 456:93-94.
Huang, "Initiation of Phase II/III Clinical Trials of Olipudase alpha for the treating Acid Sphingomyelinase Deficiency in Adults," (2016) J Int Pharm 43(5):1007.
"A Long-Term Study of Olipudase Alfa in Patients With Acid Sphingomyelinase Deficiency," ClinicalTrials.gov Identifier: NCT02004704, U.S. National Library of Medicine, (2013) Retrieved from the Internet: URL: https://classic.clinicaltrials.gov/ct2/show/NCT02004704 [Updated Jul. 21, 2023].
Wasserstein et al, "Acid Sphingomyelinase Deficiency." In: GeneReviews PMID: 20301544 (2006) pp. 1-24 [Updated Apr. 27, 2023].
European Patent Office Communication under Rule 71(3) EPC—Intention to Grant, dated Jun. 1, 2023 in EP Application No. 18 768 948.4.

* cited by examiner

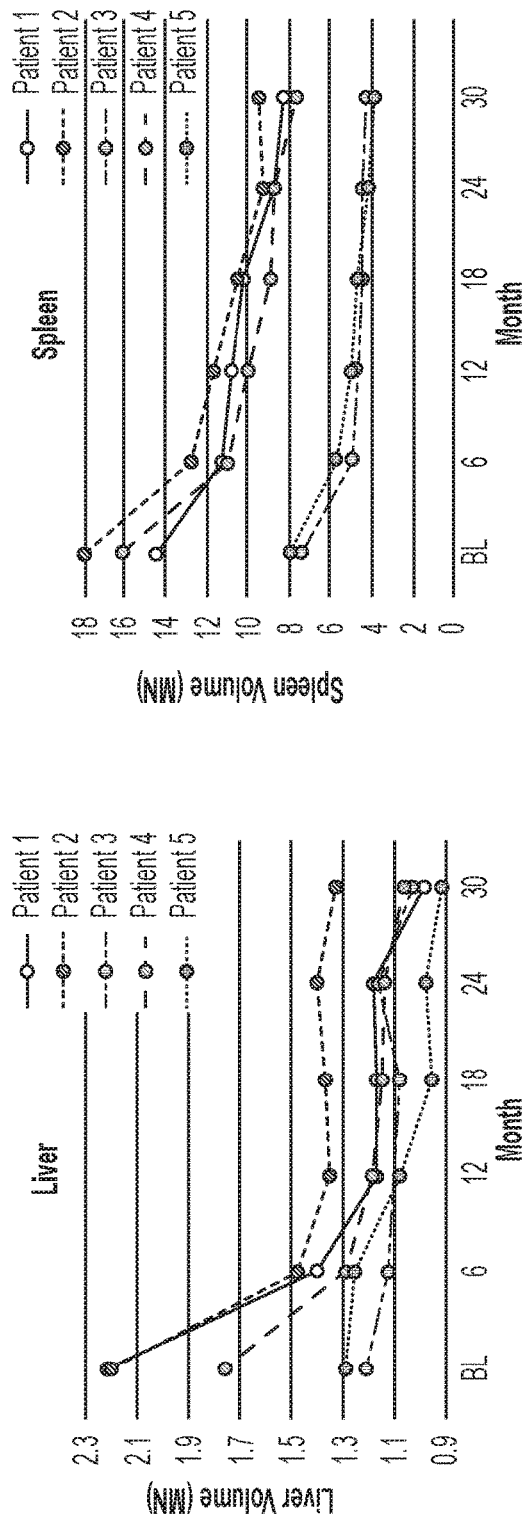
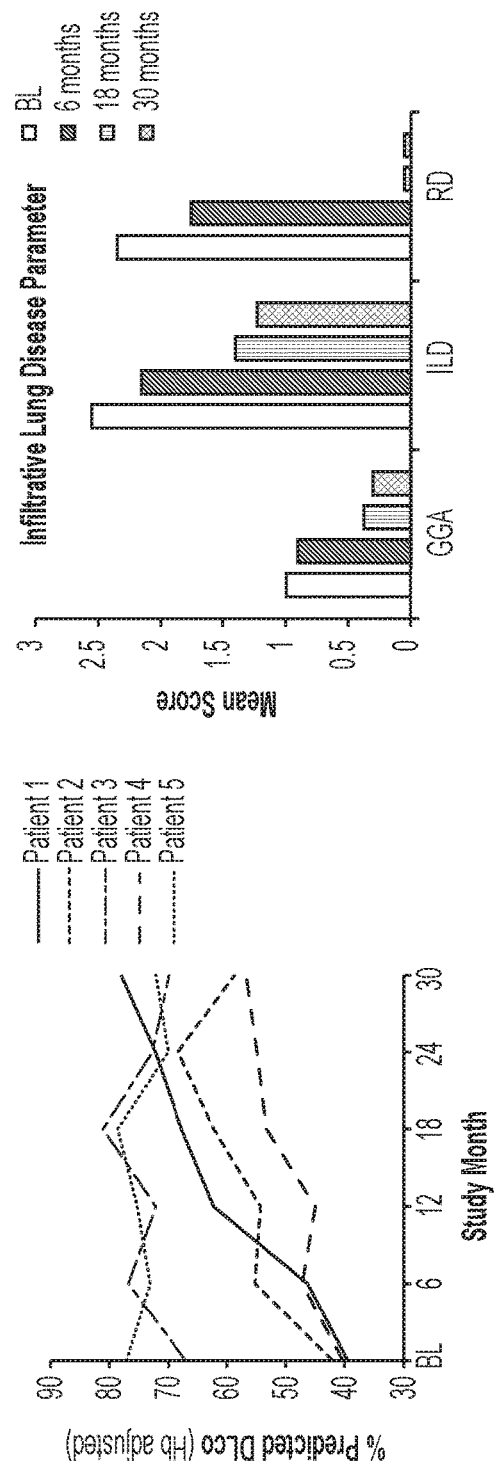
FIG. 2A
FIG. 2B

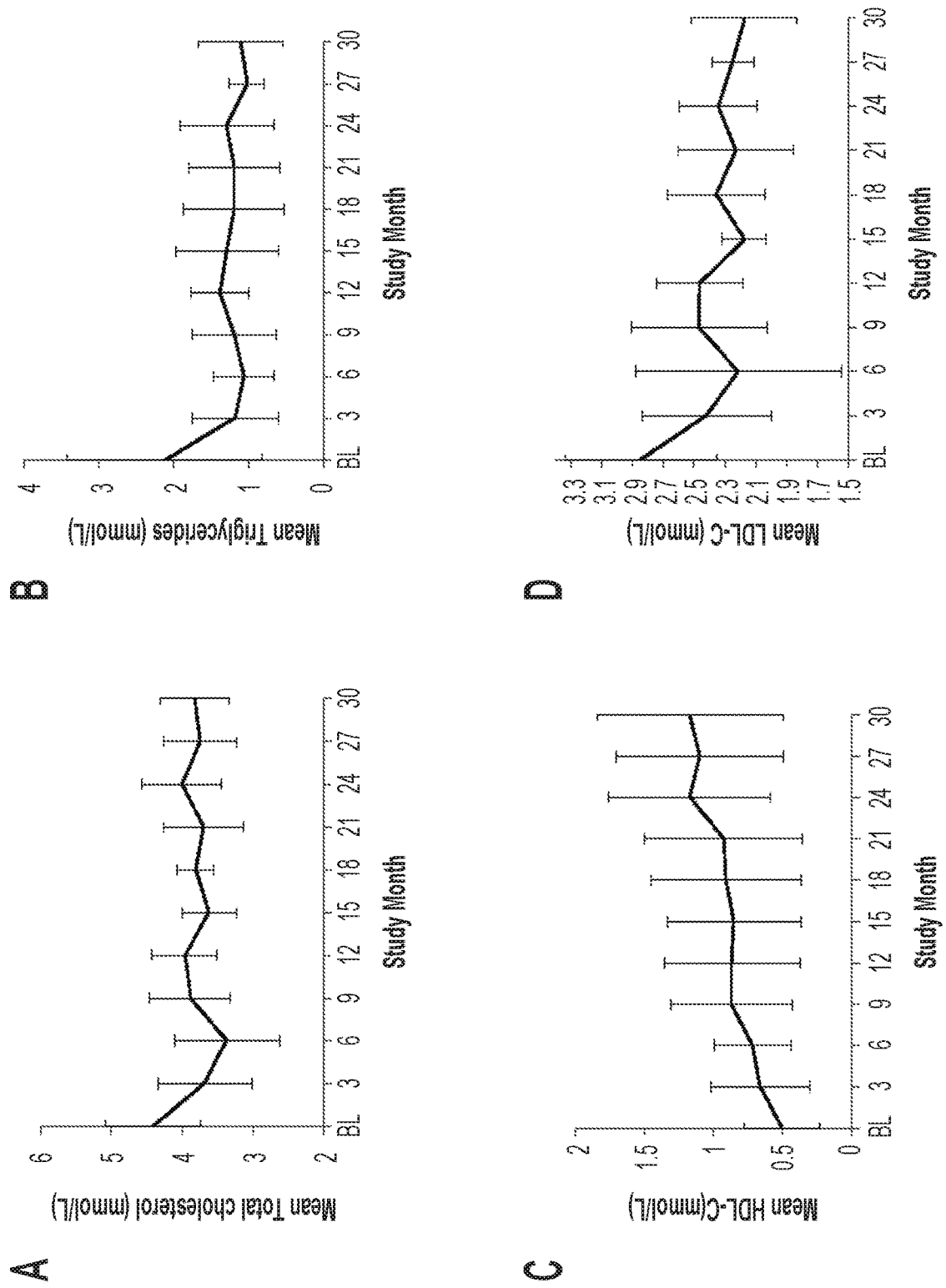
FIGS. 4A-D

TREATMENT OF ABNORMAL BONE CONDITIONS IN ACID SPHINGOMYELINASE DEFICIENCY PATIENTS

CROSS REFERENCE TO RELATED APPLICATIONS

This application is a National Stage under 35 U.S.C § 371 of International Patent Application No. PCT/IB2018/056346, filed on Aug. 22, 2018, which claims priority from U.S. Provisional Application No. 62/549,732, filed on Aug. 24, 2017, and European Application No. 17306720.8, filed on Dec. 7, 2017. The disclosures of the aforementioned priority applications are incorporated herein by reference in their entirety.

SEQUENCE LISTING

The instant application contains a Sequence Listing which has been submitted electronically in ASCII format and is hereby incorporated by reference in its entirety. Said ASCII copy, created on 10 Aug. 2018, is named 022548_WO047_SL.txt and is 21,687 bytes in size.

FIELD OF THE INVENTION

This application relates to the use of human acid sphingomyelinase in treating abnormal bone conditions in patients with acid sphingomyelinase deficiency (ASMD).

BACKGROUND OF THE INVENTION

Acid sphingomyelinase deficiency (ASMD) is a rare life-threatening lysosomal storage disorder. It is an autosomal recessive genetic disease that results from mutations in the SMPD1 gene encoding the lysosomal enzyme acid sphingomyelinase (ASM) (Schuchman et al., *Mol. Genet. Metab.* 120(1-2):27-33 (2017)). ASMD patients are unable to metabolize sphingomyelin, which as a result accumulates in lysosomes in multiple organs, causing visceral disease and neurodegeneration in severe cases. ASMD patients have increased cholesterol and other lipids in spleen, liver, lung and bone marrow.

Infantile neurovisceral ASMD (historically known as Niemann-Pick disease type A or NPD A), the most severe disease phenotype, is characterized as the early-onset and acute neuropathic form, and results in failure to thrive, hepatosplenomegaly, and rapidly progressive neurodegeneration. Patients die in early childhood (McGovern et al., *Neurology* 66(2):228-232 (2006)). Patients with chronic visceral ASMD (NPD B) and chronic neurovisceral ASMD (NPD A/B) have onset that varies from infancy to adulthood (Wasserstein et al., *Pediatrics* 114(6):e672-677 (2004); Wasserstein et al., *J. Pediatr.* 149(4):554-559 (2006)). NPD B patients are usually diagnosed in childhood, typically after the age of 2 years. Most NPD B patients live to adulthood. NPD A/B patients are classified as having an intermediate form, with manifestation of childhood neurologic symptoms that may develop as neurodegenerative disease.

Morbidity from liver, lung, and hematologic diseases occurs in all patients with chronic ASMD and includes hepatosplenomegaly, liver dysfunction, infiltrative lung disease and thrombocytopenia (McGovern et al., *Genet. Med.* 15(8):618-623 (2013); McGovern et al., *Orphanet J. Rare Dis.* 12(1):41 (2017)). Growth restriction during childhood and bone disorders such as low bone density are also common features of chronic ASMD (Wasserstein et al., *J Pediatr.* 142(4):424-428 (2003)). Pulmonary and liver diseases are the main causes of death in these patients (McGovern et al., *Pediatrics* 122(2):e341-349 (2008); Cassiman et al., *Mol. Genet. Metab.* 118(3):206-213 (2016)).

Due to the high morbidity and mortality rates of ASMD, there remains an urgent need for an effective treatment of this genetic disease.

SUMMARY OF THE INVENTION

The present invention provides a method of treating an abnormal bone condition in a patient with acid sphingomyelinase deficiency (ASMD), comprising the steps of administering to the patient a plurality of doses of recombinant human acid sphingomyelinase (rhASM), measuring a bone indicator of the patient, and comparing the bone indicator of the patient to the baseline bone indicator of the patient before the administering step, wherein the patient's bone indicator improves or does not worsen after the plurality of doses of rhASM. In some embodiments, the bone indicator is bone mineral density (BMD), wherein the BMD improves (e.g., increases) or does not worsen after the plurality of doses of rhASM. In some embodiments, the bone indicator is bone marrow burden (BMB), wherein the BMB decreases or does not increase after the plurality of doses of rhASM. In some embodiments, the bone indicator is skeletal development (e.g., bone maturation and/or linear growth), wherein the skeletal development improves after the plurality of doses of rhASM. In certain embodiments, the abnormal bone condition is osteopenia or osteoporosis.

The present invention also provides a method for decreasing bone marrow burden (BMB) in an acid sphingomyelinase deficiency patient in need thereof, comprising the steps of determining the BMB of the patient, and administering to the patient a plurality of doses of recombinant human acid sphingomyelinase (rhASM), thereby decreasing the BMB of the patient.

The present invention also provides a method for improving bone mineral density (BMD) in an acid sphingomyelinase deficiency patient in need thereof, comprising the steps of determining the BMD of the patient, and administering to the patient a plurality of doses of recombinant human acid sphingomyelinase (rhASM), thereby improving the BMD of the patient.

The present invention also provides a method for decreasing bone marrow burden (BMB) in an acid sphingomyelinase deficiency patient in need thereof, comprising the steps of selecting a patient with acid sphingomyelinase deficiency who is not receiving bisphosphonate therapy, and administering to the patient a plurality of doses of recombinant human acid sphingomyelinase (rhASM), thereby decreasing the BMB of the patient.

The present invention also provides a method for improving (e.g., increasing) bone mineral density (BMD) in an acid sphingomyelinase deficiency patient in need thereof, comprising the steps of selecting a patient with acid sphingomyelinase deficiency who is not receiving bisphosphonate therapy, and administering to the patient a plurality of doses of recombinant human acid sphingomyelinase (rhASM), thereby improving the BMD of the patient.

The present invention also provides a method of improving skeletal development (e.g., bone maturation and/or linear growth) in an acid sphingomyelinase deficiency (ASMD) patient in need thereof, comprising the steps of selecting an ASMD patient for improvement of skeletal development, and administering to the patient a plurality of doses of recombinant human acid sphingomyelinase (rhASM), thereby improving skeletal development in the patient.

The present invention also provides a method of improving or maintaining quality of life in an acid sphingomyelinase deficiency (ASMD) patient in need thereof, comprising the steps of selecting an ASMD patient for improvement of quality of life, and administering to the patient a plurality of doses of recombinant human acid sphingomyelinase (rhASM), thereby improving or maintaining quality of life in the patient.

The present invention also provides a method of treating osteopenia in an acid sphingomyelinase deficiency (ASMD) patient in need thereof, comprising the steps of selecting an ASMD patient for treatment of osteopenia, and administering to the patient a plurality of doses of recombinant human acid sphingomyelinase (rhASM).

The present invention also provides a method of treating osteoporosis in an acid sphingomyelinase deficiency patient in need thereof, comprising the steps of selecting an ASMD patient for treatment of osteoporosis, and administering to the patient a plurality of doses of recombinant human acid sphingomyelinase (rhASM).

In any of the treatment methods described herein, the plurality of doses may be administered to the patient over a period of six to thirty months. The recited effect of the rhASM plurality of doses thus is obtained in said period.

In any of the treatment methods described herein, the patient may have, e.g., chronic visceral ASMD (Niemann-Pick disease type B) or chronic neurovisceral ASMD (NPD A/B). The patient may be an adult or pediatric patient.

In any of the treatment methods described herein, the first two or more doses of rhASM may be escalating doses and may be administered at a successively increasing amount. In some embodiments, the doses after the escalating doses are maintenance doses (which may start with, e.g., the highest maintenance dose) and may be administered in the same amount as or less than the last escalating dose. In certain embodiments, the highest maintenance dose is the highest dose tolerated by the patient. The first dose may be, e.g., 0.1 mg/kg, for either adult or pediatric patients. The highest maintenance dose may be, e.g., in the amount of 0.3 mg/kg to 3 mg/kg (e.g., 1 mg/k to 3 mg/kg), such as 1 mg/kg, 2 mg/kg, or 3 mg/kg. Maintenance doses may be, e.g., in the amount of 0.1 mg/kg to 3 mg/kg, or 0.3 mg/kg to 3 mg/kg, such as, for example, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.5 mg/kg, 2 mg/kg, 2.5 mg/kg, or 3 mg/kg. In particular embodiments, the escalating doses may be administered in the order of 0.1 mg/kg, 0.3 mg/kg, 0.3 mg/kg, 0.6 mg/kg, 0.6 mg/kg, 1.0 mg/kg, 2.0 mg/kg, and 3.0 mg/kg.

In some embodiments, the plurality of doses in any of the treatment methods described herein are administered at an interval of every 2 weeks. Administration of the plurality of doses may be, e.g., through intravenous injection.

In any of the treatment methods described herein, the rhASM may be olipudase alfa (SEQ ID NO:2).

The present invention also provides the use of a recombinant human ASM (e.g., olipudase alfa) for the manufacture of a medicament for use in any of the treatment methods described herein, as well as provides a recombinant human ASM (e.g., olipudase alfa) for use in any of the treatment methods described herein.

The present invention also provides articles of manufactures (e.g., kits) containing a recombinant human ASM (e.g., olipudase alfa) for use in any of the treatment methods described herein.

BRIEF DESCRIPTION OF THE FIGURES

FIGS. 2A and 2B are graphs summarizing the effect of olipudase alfa on liver and spleen volume (A) and lung disease (B). FIG. 2A: Liver and spleen volumes were calculated by integrating cross-sectional magnetic resonance images and expressed as multiples of normal (MN) where normal spleen volume (L) was assumed to be 0.2% of body weight, and normal liver volume (L) to be 2.5% of body weight. FIG. 2B: Lung Disease. By-patient percent predicted DLco, adjusted for hemoglobin (Hb), at baseline and during treatment, were calculated using observed values for male and female patients (Crapo et al., *Am. Rev. Respir. Dis.* 123(2):185-189 (1981); Macintyre et al., *Eur. Respir. J.* 26(4):720-735 (2005)). Degree of severity: 80%=lower limit of normal; >60%-79%=mild decrease; 40%-60%=moderate decrease; <40%=severe decrease. HRCT assessment of infiltrative lung disease at baseline and during treatment with olipudase alfa included ground glass appearance (GGA), interstitial lung disease (ILD), and reticulo-nodular density (RD) scored on a 4 point system where 0=No interstitial lung disease; 1=Mild (affecting 1-25% of the lung volume); 2=Moderate (affecting 26-50% of the lung volume); 3=Severe (affecting 51-100% of the lung volume).

FIG. 3A (femur): Bone marrow burden changes in the coronal femur of Patient 2, (female, 32 years old at baseline). Proximal epiphysis bone marrow hypointensity at screening in the T1-weighted (A) and T2-weighted (B) images is compared with the reduced amount and slightly hypointense diaphyseal bone marrow following 30 months of treatment (T1-weighted, C and T2-weighted, D). Full vertical scale bar, 20 cm. FIG. 3B (spine): Bone marrow burden in the sagittal lumbar spine of Patient 2. At screening, diffuse infiltration of the bone marrow is observed with T1-weighted isointensity of the non-diseased intervertebral discs (A) and T2-weighted hyperintense signal intensity of presacral fat (B). After 30 months of treatment, the infiltration of the bone marrow remains unchanged (T1-weighted, C) while the presacral fat is improved to slightly hyperintense (T2-weighted, D). Full vertical scale bar, 20 cm.

FIGS. 4A-D are graphs depicting fasting lipid parameters at baseline and during treatment (30 months) with olipudase alfa. Mean (SD) pre-infusion fasting levels of total cholesterol (A), triglycerides (B), HDL cholesterol (C), and LDL cholesterol (D) are shown. Total cholesterol normal range: US<5.18 mmol/L; UK 0-3.9 mmol/L. HDL-C normal range: US male >0.777; US female >0.9065 mmol/L; UK >1.2 mmol/L. LDL-C normal range: US<3.3411 mmol/L; UK 0-2 mmol/L. Triglycerides normal range: <1.7 mmol/L.

DETAILED DESCRIPTION OF THE INVENTION

Figure 1A:
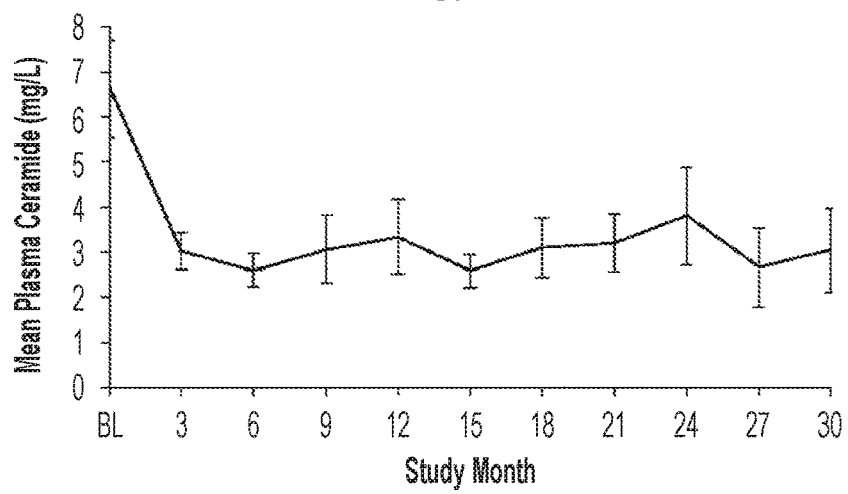
FIGS. 1A-C are graphs summarizing the changes in ceramide (A), lyso-sphingomyelin (B) and chitotriosidase (C) activity during 30 months of treatment with olipudase alfa. Normal range for plasma ceramide was 1.8-6.5 mg/L. The upper limit of normal for lyso-sphingomyelin in dried blood spots was <69 μg/L, and normal chitotriosidase serum levels were ≤181 nmol/hr/mL (note: activity was not corrected for two patients heterozygous for a chitotriosidase null mutation).

The present invention is based on the discovery that ASM enzyme replacement therapy (ERT) alleviates abnormal bone conditions in ASMD patients, including increasing their bone density and decreasing their bone marrow burden. This improvement may be seen within as few as 6-30 months of therapy. This discovery was unexpected because it was not clear whether an ASM ERT would reverse all symptoms of ASMD, including low bone density, and if so, how long it would take for the therapy to achieve the reversal of the symptoms. In other lipid storage disorders, ERT alone is very slow in improving bone mineral density. For example, in Gaucher Disease, another genetic lipid storage disorder, patients' response to treatment with ERT is slower for bone mineral density (BMD) than for hematologic and visceral aspects of GD. Studies have shown that eight years of ERT (imiglucerase) was required to restore patients' BMD to normal levels (Wenstrup et al., *J Bone Miner Res.* 22(1):119-26 (2007)). The present discovery also is significant because ASMD patients cannot take bisphosphonates, the standard-of-care medications for low BMD, while on ASM ERT, because bisphosphonates interfere with ASM activity.

Accordingly, the present invention provides methods of treating an abnormal bone condition in an ASMD patient by using ASM ERT. ASMD causes accumulation of sphingomyelin in bone marrow cells, especially precursor cells of the mononuclear-macrophage lineage. These cells become engorged and trapped in the bone marrow, causing bone marrow infiltration and a high bone marrow burden (BMB). ASMD patients often have chronic inflammation as well, including in the bones. Bone disease in ASMD adversely impacts bone metabolism and structure. Patients suffer from a number of symptoms, including growth delays, growth retardation, maturation delays, bone pain, and fractures. Indeed, ASMD has been shown to be inversely correlated with lumbar spine bone mineral density (BMD) Z-score (Wasserstein et al. *J. Inherit. Metab. Dis.* 36(1):123-7 (2013)) and to impact the skeletal system. As used herein, an abnormal bone condition or a bone disease refers to any bone issue associated with ASMD and the resulting manifestations such as high bone marrow burden, low bone mineral density, osteopenia, osteoporosis, delayed skeletal development (e.g., delayed bone age (maturation) and delayed linear growth), increased disability, bone pain, decreased mobility, osteonecrosis, and increased risk of fractures.

In some embodiments, the abnormal bone condition treated in the ASMD patient by the methods of the invention is osteopenia or osteoporosis. In some embodiments, the patients are adults (e.g., patients 18 years or older, including geriatric patients who are 65 years or older). In other embodiments, the patients are pediatric patients (patients who are younger than 18 years old, e.g., patients who are newborn to 6 years old, who are 6 to 12 years old, or who are 12 to 18 years old). In some embodiments, the patient may have Niemann-Pick Disease type A, Niemann-Pick Disease type B, or Niemann-Pick Disease type A/B. In particular embodiments, the methods described herein are used to treat adult patients with chronic visceral ASMD (NPD B). In some embodiments, the methods described herein are used to treat pediatric patients with chronic visceral ASMD (NPD B). In other embodiments, the methods described herein are used to treat adult and pediatric patients with non-neurological manifestations of ASMD.

Assessment of Bone Conditions

Bone conditions in a subject can be assessed by analyzing bone parameters, collectively referred herein as "bone indicators," using various methods. Bone indicators may comprise, e.g., bone mineral density (BMD), bone marrow burden (BMB), bone age, linear growth, and the status of certain bone biomarkers. In certain embodiments, abnormal bone conditions may be assessed by bone imaging such as X-ray imaging and magnetic resonance imaging (MRI). Bone scan images may be obtained from, for example, femur and lumbar spine at various time points to evaluate bone mineral density (BMD) and bone marrow burden (BMB) as indicators of bone condition in patients before, during, and after treatment with a composition of the present invention. In certain embodiments, the images are obtained using DXA (dual-energy X-ray absorptiometry) or MRI. In some embodiments, bone scan images may be obtained approximately every week, 2 weeks, 3 weeks, 4 weeks, 5 weeks, six weeks, month, 2 months, 3 months, 4 months, 5 months, 6 months, 7 months, 8 months, 9 months, 10 months, 11 months, year, 2 years, 3 years, 4 years, or 5 years, and compared to baseline images obtained before treatment of the present invention. In certain embodiments, the bone scan images may be obtained approximately every 6 months or every year.

BMD may be calculated for each patient using T- and Z-scores. The T-score ranks a patient's bone density compared to that of a healthy person of the same gender. The Z-score rank a patient's bone density compared to that of a healthy person of the same age, gender, weight, and ethnicity.

From serial MRI scans, BMB may be evaluated using the BMB scoring system, which relies on a bone marrow signal intensity scoring system giving a categorical score out of a possible eight points each for the lumbar spine and femur—femur scores averaged from the left and right femur—for a total score of 16 points. The bone marrow signal intensity scoring system is described in, for example, Hangartner et al., *Skeletal Radiol.* 37(3): 185-188 (2008); Robertson et al., *AJM Am J Roentgenol.* 188(6): 1521-1528 (2007); and Maas et al., *Radiology* 229(2): 554-561 (2003), all of which are incorporated herein by reference in their entirety.

In other embodiments, bone biomarkers will be analyzed to assess bone conditions of a subject. "Bone biomarkers," as used herein, refer to biomarkers associated with bone formation and resorption. For example, bone biomarkers such as serum bone-specific alkaline phosphatase (ALP) and C-telopeptide may be analyzed in samples collected from a patient. Bone-specific ALP, a marker for active bone formation, and C-telopeptide, an indicator of bone resorption, may be used as indicators of bone condition. For example, in Gaucher Disease, another lipid storage disorder, the C-telopeptide serum concentration is decreased. In some embodiments, bone biomarkers may be analyzed approximately every 1, 2, 3, 4, 5, 6, 7, 8, 9, 10, or 11 months, or every 1, 2, 3, 4, or 5 years, and compared to baseline levels obtained before treatment of the present invention. In certain embodiments, the bone biomarkers may be analyzed every 3 or 6 months.

Most children with ASMD have delayed growth. The Z scores for height and weight in ASMD pediatric patients are often lower than in children unaffected by ASMD. In ASMD pediatric patients, additional bone indicators such as bone age (e.g., as determined by hand X-ray) and linear growth may be analyzed to assess bone growth or skeletal development. In an exemplary embodiment, hand X-ray may be performed to collect images of the patients' hands, fingers and wrists. Bone age (maturation) may be calculated from the X-ray using the Greulich & Pyle Atlas (1959). Linear growth, as measured by height Z-score, is another bone indicator to assess growth in pediatric patients.

Treatment of Abnormal Bone Conditions with ASM

Patients with abnormal bone conditions, such as ASMD patients, can be treated with ASM ERT. As used herein, "treat," "treating" and "treatment" refer to a method of alleviating, abrogating, or preventing or delaying the onset or worsening (i.e., progression) of a biological disorder or condition and/or at least one of its attendant symptoms. As used herein, to "alleviate" a disease, disorder or condition means reducing the severity and/or occurrence frequency of the symptoms of the disease, disorder, or condition.

In some embodiments, the ASM used in the ASM ERT may be human ASM, e.g., a recombinant human ASM (rhASM). The recombinant ASM may be produced using recombinant technology in prokaryotic or eukaryotic host cells such as mammalian host cells (e.g., Chinese hamster ovary (CHO) cells). In certain embodiments, the rhASM is olipudase alfa, the glycoform alpha of a human ASM (EC-3.1.4.12) produced in CHO cells. Mature olipudase alfa is a 570 amino acid polypeptide that retains the enzymatic and lysosomal targeting activity of the native human protein. The amino acid sequence of olipudase alfa, including its leader sequence (residues 1-57), is shown below, where the leader sequence is italicized and in boldface. The mature olipudase alfa sequence (SEQ ID NO:2, which spans residues 58-627 of the following sequence) does not have the leader sequence.

```
                                          (SEQ ID NO: 1)
MARYGASLRQ SCPRSGREQG QDGTAGAPGL LWMGLALALA

LALALSDSRV LWAPAEAHPL SPQGHPARLH RIVPRLRDVF

GWGNLTCPIC KGLFTAINLG LKKEPNVARV GSVAIKLCNL

LKIAPPAVCQ SIVHLFEDDM VEVWRRSVLS PSEACGLLLG

STCGHWDIFS SWNISLPTVP KPPPKPPSPP APGAPVSRIL

FLTDLHWDHD YLEGTDPDCA DPLCCRRGSG LPPASRPGAG

YWGEYSKCDL PLRTLESLLS GLGPAGPFDM VYWTGDIPAH

DVWHQTRQDQ LRALTTVTAL VRKFLGPVPV YPAVGNHEST

PVNSFPPPFI EGNHSSRWLY EAMAKAWEPW LPAEALRTLR

IGGFYALSPY PGLRLISLNM NFCSRENFWL LINSTDPAGQ

LQWLVGELQA AEDRGDKVHI IGHIPPGHCL KSWSWNYYRI

VARYENTLAA QFFGHTHVDE FEVFYDEETL SRPLAVAFLA

PSATTYIGLN PGYRVYQIDG NYSGSSHVVL DHETYILNLT

QANIPGAIPH WQLLYRARET YGLPNTLPTA WHNLVYRMRG

DMQLFQTFWF LYHKGHPPSE PCGTPCRLAT LCAQLSARAD

SPALCRHLMP DGSLPEAQSL WPRPLFC
```

In some embodiments, the ASM is 99%, 98%, 97%, 96%, or 95% identical in amino acid sequence to olipudase alfa. For example, an ASM useful in the present invention has the ASM sequence shown in U.S. Pat. No. 6,541,218, the disclosure of which is incorporated herein in its entirety. That sequence is shown below, with the leader sequence italicized and boldfaced, where the mature protein does not have the leader sequence:

```
                                          (SEQ ID NO: 3)
MPRYGASLRQ SCPRSGREQG QDGTAGAPGL LWMGLVLALA

LALALALSDS RVLWAPAEAH PLSPQGHPAR LHRIVPRLRD

VFGWGNLTCP ICKGLFTAIN LGLKKEPNVA RVGSVAIKLC

NLLKIAPPAV CQSIVHLFED DMVEVWRRSV LSPSEACGLL

LGSTCGHWDI FSSWNISLPT VPKPPPKPPS PPAPGAPVSR

ILFLTDLHWD HDYLEGTDPD CADPLCCRRG SGLPPASRPG

AGYWGEYSKC DLPLRTLESL LSGLGPAGPF DMVYWTGDIP

AHDVWHQTRQ DQLRALTTVT ALVRKFLGPV PVYPAVGNHE

SIPVNSFPPP FIEGNHSSRW LYEAMAKAWE PWLPAEALRT

LRIGGFYALS PYPGLRLISL NMNFCSRENF WLLINSTDPA

GQLQWLVGEL QAAEDRGDKV HIIGHIPPGH CLKSWSWNYY

RIVARYENTL AAQFFGHTHV DEFEVFYDEE TLSRPLAVAF

LAPSATTYIG LNPGYRVYQI DGNYSRSSHV VLDHETYILN

LTQANIPGAI PHWQLLYRAR ETYGLPNTLP TAWHNLVYRM

RGDMQLFQTF WFLYHKGHPP SEPCGTPCRL ATLCAQLSAR

ADSPALCRHL MPDGSLPEAQ SLWPRPLFC
```

An ASM useful in the present invention may also be identical in amino acid sequence to the human ASM disclosed in the UNIPROT database as sequence P17405-1, or polymorphic variants thereof. The P17405-1 sequence is shown below, with the leader sequence italicized and boldfaced, where the mature protein does not have the leader sequence:

```
                                          (SEQ ID NO: 4)
MPRYGASLRQ SCPRSGREQG QDGTAGAPGL LWMGLVLALA

LALALSDS RVLWAPAEAH PLSPQGHPAR LHRIVPRLRD

VFGWGNLTCP ICKGLFTAIN LGLKKEPNVA RVGSVAIKLC

NLLKIAPPAV CQSIVHLFED DMVEVWRRSV LSPSEACGLL

LGSTCGHWDI FSSWNISLPT VPKPPPKPPS PPAPGAPVSR

ILFLTDLHWD HDYLEGTDPD CADPLCCRRG SGLPPASRPG

AGYWGEYSKC DLPLRTLESL LSGLGPAGPF DMVYWTGDIP

AHDVWHQTRQ DQLRALTTVT ALVRKFLGPV PVYPAVGNHE

STPVNSFPPP FIEGNHSSRW LYEAMAKAWE PWLPAEALRT

LRIGGFYALS PYPGLRLISL NMNFCSRENF WLLINSTDPA

GQLQWLVGEL QAAEDRGDKV HIIGHIPPGH CLKSWSWNYY

RIVARYENTL AAQFFGHTHV DEFEVFYDEE TLSRPLAVAF

LAPSATTYIG LNPGYRVYQI DGNYSGSSHV VLDHETYILN

LTQANIPGAI PHWQLLYRAR ETYGLPNTLP TAWHNLVYRM

RGDMQLFQTF WFLYHKGHPP SEPCGTPCRL ATLCAQLSAR

ADSPALCRHL MPDGSLPEAQ SLWPRPLFC
```

Proof of concept for olipudase alfa therapy was demonstrated in an ASM knock-out (ASMKO) mouse model (See, e.g., Miranda et al., *FASEB* 14 (13):1988-95 (2000); Dhami et al., *Lab. Inves.* 81(7): 987-99 (2001)). Those studies showed that repeated intravenous administration of olipudase to ASMKO mice led to dose-dependent reduction of sphingomyelin in visceral organs. Sphingomyelin reduction was also observed in the lungs. The ASMKO studies also showed that olipudase alfa may cause toxicity when given in high doses. However, when the ASMKO mice were given multiple low doses followed by a high dose, olipudase alfa did not cause the toxicity observed with a single high dose.

Olipudase alfa has been used in clinical studies for the treatment of non-neurologic ASMD manifestations. The observations in mice led to the development of a Phase 1 study to evaluate the safety and pharmacokinetics of olipudase alfa treatment, in which single, ascending doses of olipudase alfa (0.03, 0.1, 0.3, 0.6 and 1.0 mg/kg) were evaluated in 11 patients (McGovern et al., *Genet. Med.* 15(8):618-623 (2013) and WO 2011/025996; the disclosures of which are incorporated herein by reference in their entirety). The patients in that study showed dose-related increases in acute phase reactants including ceramide, bilirubin, and high sensitivity C-reactive protein (hsCRP). Dose-related adverse events involving constitutional symptoms (pain, fever, nausea, and vomiting) consistent with first-dose toxicity were also reported.

A Phase 1b study to evaluate the safety and tolerability of olipudase alfa during a 26-week treatment period was conducted with 5 adult patients (Wasserstein et al., *Mol. Genet. Metab.* 116(1-2):88-97 (2015), incorporated herein by reference in its entirety). The patients in this study were given olipudase alfa in a dose-escalated manner with an initial dose of 0.1 mg/kg followed by stepwise biweekly increases to reach the target dose of 3.0 mg/kg. The study showed that the dose escalation regimen was well tolerated with no serious or severe adverse events, and resulted in gradual debulking of sphingomyelin and its catabolites. Debulking refers to the removal of sphingomyelin that has been accumulated in a patient's visceral organs due to ASMD. Improvements observed in the patients included decreased spleen and liver volumes, decreased interstitial lung disease scores, increased lung function, and reduction in serum chitotriosidase, CCL18, ACE, and other disease biomarkers. The inventors have now found that when these patients continued to be treated and monitored for 30 months in a long-term safety and efficacy assessment, they showed sustained safety profile and continued improvement in clinically relevant parameters, including spleen and liver volumes, lung disease score, lipid profiles, and ASM biomarkers. The inventors have also unexpectedly found that the patients displayed marked improvement in bone mineral density (BMD) and bone marrow burden (BMB). These data demonstrate that ASM ERT can alleviate or prevent the worsening of a patient's abnormal bone condition such as osteopenia and osteoporosis.

Dosage and Route of ASM Administration

Pharmaceutical compositions comprising an ASM as described herein will be administered in a therapeutically effective amount for treatment of the condition in question (e.g., an ASMD-associated abnormal bone condition), i.e., at dosages and for periods of time necessary to achieve a desired result. A therapeutically effective amount may vary according to factors such as the particular condition being treated, the age, sex, and weight of the patient, and whether the enzyme replacement therapy is being administered as a stand-alone treatment or in combination with one or more additional treatments. "Therapeutically effective amount" refers to the amount of the therapeutic agent being administered that will relieve to some extent or prevent the worsening of one or more of the symptoms of the disorder or condition being treated. The ASM compositions may be administered through intravenous injection.

In some embodiments, efficacy may be indicated as improvement in bone mineral density T-scores (e.g., spinal and/or femur T-scores). In certain embodiments, the T-score is improved by at least 0.5 points. In some embodiments, efficacy may be indicated as improvement in bone mineral density Z-scores (e.g., spinal and/or femur Z-scores). In certain embodiments, the Z-score is improved by at least 0.1 points. In some embodiments, efficacy may be indicated as improvement, non-worsening, or a delay in progression of bone diseases such as osteopenia or osteoporosis. In some embodiments, efficacy may be indicated by improvements in skeletal development such as linear growth or bone age (maturation). In certain embodiments, the improvement in skeletal development may be measured against data collected from study of pediatric patients (Wasserstein et al., *J Pediatr* 142(4):424-428 (2003)). In other embodiments, improvement in skeletal development may be measured against each patient's growth chart before ASM therapy.

In some embodiments, the methods of the invention involve a dose escalation protocol in which increasing doses of ASM (e.g., an rhASM such as olipudase alfa) are administered over an appropriate period to gradually debulk previously accumulated sphingomyelin and to minimize toxic side effects caused by sphingomyelin catabolites. For example, treatment may involve the administration of one or more initial, low, non-toxic doses of ASM to a patient to reduce the amount of sphingomyelin that has accumulated in the patient. Each escalating dose may be separated from the previous dose by one week, two weeks, or three weeks. In particular embodiments, the escalating doses are given two weeks apart. As used herein, the term "non-toxic dose(s)" and the like refers to a dosage of an ASM administered to ASMD patients without resulting in one, two, three or all of the following: (i) a moderate or severe related adverse event as defined by a clinical symptom that interferes with normal daily functioning and requires additional monitoring, intervention, or treatment, or, an abnormal laboratory value or procedural result of clinical concern that requires further monitoring, treatment, or investigation. See, e.g., the Clinical Data Interchange Standards Consortium Study Data Tabulation Model standard terminology v. 3.1.1; (ii) a total bilirubin value of greater than 1.5 mg/dL, 2 mg/dL, 3 mg/dL, or 4 mg/dL, that lasts for greater than one week, two weeks or three weeks after administration of a dose of rhASM; (iii) a plasma ceramide concentration of greater than 8.2 µg/dL, 9 µg/dL, 10 µg/dL, 15 µg/dL, 20 µg/dL, 30 µg/dL, 40 µg/dL, 50 µg/dL, 60 µg/dL, 70 µg/dL, or 80 µg/dL, 24 hours, 36 hours, 48 hours or 72 hours after administration of the dose of ASM; or (iv) an acute phase response/reaction. The "non-toxic dose" of ASM may vary depending upon, e.g., the stability of the enzyme used, the activity of the enzyme used, and/or the route of administration of the enzyme. For example, the dosage of a modified ASM enzyme with increased activity may be lower than the dosage of an unmodified ASM. One skilled in the art would be able to adjust the dose of enzyme administered based on the stability of the enzyme, the activity of the enzyme, and/or the route of administration of the enzyme.

After a certain period of time, the dose of ASM can be escalated until the highest therapeutically effective dosage tolerated by the patient is achieved. Once this dosage is identified, it can be used as a maintenance dose to treat the patient. Alternatively, the maintenance dose may be reduced from the highest escalating dose once the patient's ASMD condition has stabilized after the dose escalation regimen.

Maintenance doses can be administered every 1, 2, 3, or 4 weeks to the patient. In certain embodiments, the maintenance dose is administered biweekly.

As used herein, the term "maintenance dose" refers to a dosage of an ASM described herein administered to ASMD patients to maintain the desired therapeutic effect, e.g., an improvement or non-worsening in one or more abnormal bone conditions such as those described herein. In specific embodiments, the maintenance dose(s) maintains one, two, three, four or more of the following desired therapeutic effects: (i) a reduction in spleen volume as assessed by techniques known in the art, e.g., MRI; (ii) a reduction in liver sphingomyelin levels as assessed by techniques known in the art, e.g., biochemical analysis and/or histomorphometric analysis of liver samples; (iii) an increase in exercise capacity as assessed by techniques known in the art, e.g., maximum workload by cycle ergometry, including percent predicted maximum workload, peak oxygen consumption and carbon dioxide production; (iv) an increase in pulmonary function as assessed by techniques known in the art, e.g., techniques described in American Thoracic Society, *Am. Rev. Respir. Dis.* 144: 1202-1218 (1991), such as diffusing capacity (DLco), percent predicted forced vital capacity (FVC) as measured by, e.g., spirometric techniques, forced expiratory volume within 1 second (FEV1) as measured by, e.g., spirometric techniques, and total lung capacity; (v) a decrease in bronchial alveolar lavage (BAL) sphingomyelin; (vi) a decrease in liver volume as assessed by techniques known in the art, e.g., MRI: (vii) an improvement in lung appearance as assessed by techniques known in the art, e.g., high resolution computed tomography (CT) scan or chest X-ray; (viii) a decrease in sphingomyelin or lyso-sphingomyelin concentration in the liver, skin, plasma and dried blood spot (DBS) as measured by, e.g., tandem mass spectrometry; (ix) a reduction or the amelioration of the severity of ASMD and/or a symptom associated therewith; (x) a reduction in the duration of a symptom associated with ASMD; (xi) the prevention in the recurrence of a symptom associated with ASMD; (xii) a reduction in hospitalization of a subject; (vi) a reduction in hospitalization length; (xiii) an increase in the survival of a subject; (xiv) a reduction in mortality; (xv) a decrease in hospitalization rate; (xvi) a reduction in the number of symptoms associated with ASMD; (xvii) an increase in symptom-free survival of ASMD patients; (xviii) an improvement in neurological function (e.g., psychomotor function, social responsiveness, etc.); (xix) an improvement in lung clearance as measured by, e.g., BAL cell count and profile; (xx) a decrease in serum levels of chitotriosidase; (xxi) a decrease in serum levels of chemokine (c-c) motif ligand 18 (CCL18); (xxii) an improvement in lipid profile (e.g., HDL, LDL, cholesterol, triglycerides, and total cholesterol:HDL ratio); (xxiii) an improvement in abnormal bone conditions; and (xxiv) improved quality of life (QOL) as assessed by, e.g., a questionnaire such as the Brief Fatigue Inventory (BFI) (Mendoza et al., *Cancer* 85(5):1186-1196 (1999)), Brief Pain Inventory-Short Form (BPI-SF) (Cleeland C., *Acta Paediatr.* Suppl. 91(439):43-47 (2002)), or Pediatric Quality of Life (PedsQL) questionnaire (Varmi et al., *Medical Care* 39(8):800-812 (2001)), or PedsQL Multidimensional fatigue scale (Varmi et al., *J Rheumatol* 31(12):2494-2500 (2004)). In certain embodiments, the highest maintenance dose is the highest or maximum dose tolerated by a patient.

In some embodiments, a patient receiving a maintenance dose is monitored every 1, 2, 3, 4, 5, 6, 7, 8, 9, 10, or 11 months, or every year or every two years for one or more of the following: (i) related adverse events; (ii) total/direct/indirect bilirubin concentrations; (iii) plasma ceramide concentration; or (iv) an acute phase response. In some embodiments, the patient is monitored every 3 months, every 6 months, or yearly. If the patient experiences a related adverse event of moderate intensity, a total bilirubin concentration greater than the total bilirubin value for a human without ASMD (e.g., a healthy human), a plasma ceramide concentration greater than the plasma ceramide concentration of a human without ASMD (e.g., a healthy human), or an acute phase response, then the dose administered to the patient can be evaluated by a physician or other medical professional to determine whether the dose should be adjusted.

In certain embodiments, a method for treating a human patient having ASMD comprises: (a) a dose-escalation regimen (e.g., for debulking accumulated sphingomyelin substrate in the human patient) comprising: (i) administering an initial dose (e.g., a low non-toxic dose such as 0.1 mg/kg) of an ASM (e.g., olipudase alfa) as described herein to the human patient; (ii) administering successively higher doses of the ASM to the human patient, and (iii) monitoring the patient for one or more adverse side effects after each successive dose as indicated by, e.g., elevated total bilirubin concentration, elevated plasma ceramide concentration, lyso-sphingomyelin, chitotriosidase, the production of acute phase reactants, the production of inflammatory mediators, or an adverse event (e.g., as defined by the Clinical Data Interchange Standards Consortium Study Data Tabulation Model standard terminology v. 3.1.1); and (b) a maintenance regimen comprising administering a dose equal to or less than the highest dose tolerated by the patient (e.g., equal or less than 3 mg/kg) as the maintenance dose for the patient.

In certain embodiments, a method for treating a human patient having ASMD, comprises: (a) a dose-escalation regimen (e.g., for debulking accumulated sphingomyelin substrate in the human patient) comprising: (i) administering an initial dose (e.g., a low non-toxic dose such as 0.1 mg/kg) of an ASM (e.g., olipudase alfa) as described herein to the human patient; (ii) administering successively higher doses of the ASM to the human patient if the patient does not manifest one or more adverse side effects as indicated by, e.g., elevated total bilirubin concentration, elevated plasma ceramide concentration, the production of acute phase reactants, lyso-sphingomyelin, chitotriosidase, the production of inflammatory mediators, or an adverse event (e.g., as defined by the Clinical Data Interchange Standards Consortium Study Data Tabulation Model standard terminology v. 3.1.1); and (b) a maintenance regimen comprising repeated administration of a maintenance dose that is equal to or less than the highest dose tolerated by the patient (e.g., equal or less than 3 mg/kg). In some embodiments, the patient is monitored for a period of time after administration of a dose of ASM (e.g., 6 hours, 12 hours, 16 hours, 24 hours, 48 hours, 72 hours, weekly, or up until the next dose) for one or more adverse side effects. In certain embodiments, the maintenance dose that is administered may be adjusted during the course of treatment of the patient. In some embodiments, the highest maintenance dose administered to the patient is the highest dose tolerated by the patient.

In certain embodiments, the initial dose ranges from 0.025 to 0.275 mg/kg, e.g., 0.03 mg/kg to 0.5 mg/kg, 0.01 to 0.5 mg/kg, or 0.1 mg/kg to 1 mg/kg, of ASM (e.g., olipudase alfa). In particular embodiments, the initial dose is 0.03 mg/kg or 0.1 mg/kg. For example, the initial dose for a pediatric patient may be 0.03 mg/kg; and the initial dose for an adult patient may be 0.1 mg/kg. In some embodiments, the initial dose for a pediatric or adult patient may be 0.1 mg/kg.

In certain embodiments, the patients will be given the same dose of olipudase alfa at least twice before escalation to a next higher dose. In some embodiments, the successively higher doses are administered one, two, three or four weeks after the previous dose. In some specific embodiments, the successively higher doses are each administered two weeks after the previous dose. In particular embodiments, the successively higher dose is 0.05-1.0 mg/kg, 0.1-3.0 mg/kg, or 0.5-2.0 mg/kg higher than the previous dose, e.g., approximately 0.07 mg/kg, 0.2 mg/kg, 0.3 mg/kg, 0.4 mg/kg, or 1 mg/kg higher than the previous dose.

In some embodiments, the highest therapeutically effective dose tolerated by a patient is 1 mg/kg to 2.5 mg/kg, 2 mg/kg to 3 mg/kg, 3 mg/kg to 5 mg/kg. In some embodiments, the highest therapeutically effective dose tolerated by a patient is 1 mg/kg, 2 mg/kg, 3 mg/kg, 4 mg/kg, or 5 mg/kg. In certain embodiments, the highest dose tolerated by the patient is 1 mg/kg to 3 mg/kg, e.g., 1 mg/kg to 2.5 mg/kg. In some embodiments, the highest dose is administered to the human patient as the highest maintenance dose. In certain embodiments, the highest maintenance dose is in the amount of, e.g., 0.3 mg/kg, 0.6 mg/kg, 1 mg/kg, 2 mg/kg or 3 mg/kg. In particular embodiments, the highest maintenance dose is 3 mg/kg. Subsequent maintenance doses may be administered in the same amount or less than the highest maintenance dose. In some embodiments, the maintenance doses are 0.3-3 mg/kg.

In some embodiments, the dose escalation regimen may entail administering the ASM in a plurality of doses in the order of, for example, 0.1 mg/kg, 0.3 mg/kg, 0.3 mg/kg, 0.6 mg/kg, 0.6 mg/kg, 1.0 mg/kg, 2.0 mg/kg, and 3.0 mg/kg (highest maintenance dose), where the successive doses are each administered two weeks after the previous dose. In other embodiments, the dose escalation regimen may entail administering the ASM in a plurality of doses in the order of, for example, 0.03 mg/kg, 0.1 mg/kg, 0.3 mg/kg, 0.3 mg/kg, 0.6 mg/kg, 0.6 mg/kg, 1.0 mg/kg, 2.0 mg/kg, and 3.0 mg/kg (highest maintenance dose), where the successive doses are each administered two weeks after the previous dose.

In certain embodiments, a dose of an ASM as described herein is administered every week, every 2 weeks, every 3 weeks, or every 4 weeks to a patient. In particular embodiments, the doses are administered at an interval of every two weeks, through, e.g., intravenous injection.

In some embodiments, the methods of the invention involve administration of the ASM doses over a period of 6 to 30 months, e.g., over a period of no more than 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 29 months, or 30 months, for the targeted bone condition(s) to improve. In certain embodiments, the ASM doses are administered over a period of no more than 30 months.

In additional embodiments, the methods of the invention involve dosing protocols and/or routes of administration as described in, e.g., WO 2011/025996, the disclosure of which is herein incorporated by reference in its entirety.

In particular embodiments, the dose escalation regimen used to treat adult or pediatric ASMD patients may be, e.g., as shown in the table below:

TABLE 1

Dose Escalation Schedule

| Treatment week | Dose of olipudase alfa (mg/kg) |
|---|---|
| 0 | 0.1 |
| 2 | 0.3 |
| 4 | 0.3 |
| 6 | 0.6 |
| 8 | 0.6 |
| 10 | 1.0 |
| 12 | 2.0 |
| 14 | 3.0 |
| 16 | 3.0 |

In further particular embodiments, the dose escalation regimen used to treat pediatric ASMD patients may be, e.g., as shown in the table below:

TABLE 2

Dose Escalation Schedule for Pediatric Patients

| Treatment week | Dose of olipudase alfa (mg/kg) |
|---|---|
| 0 | 0.03 |
| 2 | 0.1 |
| 4 | 0.3 |
| 6 | 0.3 |
| 8 | 0.6 |
| 10 | 0.6 |
| 12 | 1.0 |
| 14 | 2.0 |
| 16 | 3.0 |

In some embodiments, the pediatric patient populations include ASMD adolescent cohort (ages 12 to <18 years), ASMD child cohort (ages 6 to <12 years) and infant/early child cohort (birth to <6 years).

Articles of Manufacture and Kits

The present invention also provides articles of manufacture and kits comprising an ASM as described herein. In some embodiments, the articles and kits are suitable for treating a patient as described herein, e.g., a patient with ASMD. For example, the articles and kits may be suitable for treating an abnormal bone condition described herein in a patient with ASMD. In some embodiments, the pharmaceutically active ingredients in the articles and kits are prepared for administration at doses described herein, and are formulated for administration by methods described herein.

Unless otherwise defined herein, scientific and technical terms used in connection with the present invention shall have the meanings that are commonly understood by those of ordinary skill in the art. Exemplary methods and materials are described herein, although methods and materials similar or equivalent to those described herein can also be used in the practice or testing of the present invention. In case of conflict, the present specification, including definitions, will control. Generally, nomenclature used in connection with, and techniques of, cell and tissue culture, molecular biology, immunology, microbiology, genetics, analytical chemistry, synthetic organic chemistry, medicinal and pharmaceutical chemistry, and protein and nucleic acid chemistry and hybridization described herein are those well-known and commonly used in the art. Enzymatic reactions and purification techniques are performed according to manufacturer's specifications, as commonly accomplished in the art or as described herein. All publications and other references mentioned herein are incorporated by reference in their entirety. Although a number of documents are cited herein, this citation does not constitute an admission that any of these documents forms part of the common general knowledge in the art. Further, unless otherwise required by context, singular terms shall include pluralities and plural terms shall include the singular. Throughout this specification and embodiments, the words "have" and "comprise," or variations such as "has," "having," "comprises," or "comprising," will be understood to imply the inclusion of a stated integer or group of integers but not the exclusion of any other integer or group of integers.

In order that this invention may be better understood, the following examples are set forth. These examples are for purposes of illustration only and are not to be construed as limiting the scope of the invention in any manner.

EXAMPLE

Example 1: Long-Term Study to Assess the Safety and Efficacy of Olipudase Alfa in Patients with ASMD Patients and Study Design The objective of the study is to obtain information on the safety and efficacy of olipudase alfa in patients with ASMD following long-term administration. This ongoing, open-label, long-term study (LTS) (NCT02004704; EudraCT Number: 2013-000051-40) follows 5 adult patients with chronic ASMD who previously participated in the Phase 1b study (Wasserstein et al. *Mol Genet Metab* 116(1-2):88-97 (2015)). Data were analyzed for all patients after 30 months of treatment. The Institutional Review Board or Ethics Committee at each site approved the protocol and all patients provided written informed consent. The study was conducted according to Good Clinical Practice and in accordance with the principles of the Declaration of Helsinki.

Eligibility criteria for the Phase 1b study were previously described. Id. Patients completing the Phase 1b study with an acceptable safety profile were eligible to continue in the LTS and continued at the same olipudase alfa dose they were receiving at the end of the Phase 1b study.

Outcome Measures and Analyses

Safety assessments included standard hematologic and chemistry panels and continuous AE monitoring, including infusion associated reactions (IARs) as previously described in McGovern et al. *Genet Med* 18(1):34-40 (2015) and Wasserstein et al. *Mol. Genet. Metab.* 116(1-2):88-97 (2015). Sphingomyelin and catabolite plasma ceramide were assessed by liquid chromatography-tandem mass spectrometry (LC/MS/MS). Bone condition biomarkers also included chitotriosidase (serum) and lyso-sphingomyelin [dried blood spot (DBS)] determined by LC/MS/MS. Development of anti-drug antibodies was assessed as previously described in McGovern et al., 2015, supra, and Wasserstein et al. *Mol. Genet. Metab.* 116(1-2):88-97 (2015).

Quantitative measurements of spleen and liver volumes were determined from abdominal MRI and organ volumes were expressed as multiples of normal (MN). Percent predicted, hemoglobin-adjusted, diffusing capacity of the lung for carbon monoxide (DLco) was calculated using standardized formulas (Crapo and Morris *Am Rev Respir Dis* 123 (2):185-189 (1981), Macintyre et al. *Eur Respir J* 26(4): 720-735 (2005)). High-resolution computed tomography (HRCT) assessed infiltrative lung disease. Lung field HRCT images were scored subjectively for ground glass appearance (GG), interstitial lung disease (ILD), and reticulonodular density (RND) from 0 (no disease) to 3 (severe disease) as previously described in McGovern et al., 2015, supra, and Wasserstein et al., 2015, supra.

Fasting plasma lipid profiles, including measurement of total cholesterol (TC), low density lipoprotein (LDL-C), high density lipoprotein (HDL-C), and triglycerides, were measured throughout the study. Non-HDL levels were calculated post-hoc as the difference between total cholesterol and HDL-cholesterol levels (Jacobson et al., *J Clin. Lipidol.* 9(2):129-169 (2015)).

Bone marrow burden (BMB) was determined from MRIs of lumbar spine and both femurs, where image quantification indicated the degree of bone marrow infiltration by lipid-loaded cells (Robertson et al, *AIR. Am. J. Roentgenol.* 188(6):1521-1528 (2007)). Bone mineral density (BMD) was determined from dual-energy X-ray absorptiometry (DXA) bone scan images of lumbar spine and both femurs and determination of T- and Z-scores (WHO *JAMA* 285(6): 785-795 (2001)). BMD was assessed using the guidance provided by the International Society for Clinical Densitometry (ISCD 2015).

Patient reported outcomes using 11 point scales from 0 (absence) to 10 (worst) included the validated Brief Fatigue Inventory (BFI) (Mendoza et al., *Cancer* 85(5):1186-1196 (1999)); and Brief Pain Inventory-Short Form (BPI-SF) questionnaires to assess interference with daily activities at baseline and periodically throughout treatment (Cleeland C., *Acta Paediatr. Suppl.* 91(439):43-47 (2002)).

Statistical Methods

Descriptive statistics were provided for categorical and continuous variables, change from baseline and percent change from baseline were calculated for organ volumes and DLco, and differences determined by paired t-test and the Wilcoxon-Mann-Whitney test.

Patients and Exposure

All five adult patients (3 male and 2 female Caucasian patients) who completed the Phase 1b study continued treatment in the LTS. At baseline, all patients had splenomegaly (range 7.4 to 16.1 MN), hepatomegaly (range 1.2 to 2.2 MN), impaired gas exchange (range 43 to 80% of predicted DLco), and a pro-atherogenic lipid profile. Patient characteristics have been previously published (Wasserstein et al. *Mol. Genet. Metab.* 116(1-2):88-97 (2015)) and are summarized in Table 3. The majority of patients (4/5) remained at the 3 mg/kg olipudase alfa target dose through 30 months of treatment. For Patient 2, dose was reduced to 2 mg/kg for 6 months (months 12-18) and then to 1 mg/kg (months 18-current) due to AEs which are described below.

TABLE 3

Patient Demographics and Baseline Characteristics (Wasserstein et al., 2015)

| | Patient ID | | | | | |
|---|---|---|---|---|---|---|
| | 1 Male | 2. Female | 1 Female | 4 Male | 5 Male | Mean (SD) |
| ASMD Symptom onset age (yeam) | 2 | 1 | 6 | 0 | 12 | 4.2 (4.9) |
| ASMD Diagnosis age (years) | 2 | 2 | 12 | 8 | 12 | 7.2 (5.0) |
| Age at first olipadase alfa infusion (years) | 31 | 32 | 47 | 28 | 22 | 32.6 (9.4) |
| Spleen Volume (MN)$^a$ | 14.49 | 17.92 | 7.41 | 16.07 | 7.96 | 12.77 (4.81) |
| Liver Volume (MN)$^a$ | 2.23 | 2.20 | 1.21 | 1.76 | 1.29 | 1.74 (0.48) |
| $DL_{co}$ (% predicted)$^b$ | 43.7 | 48.0 | 77.0 | 43.0 | 80.0 | 58.3 (18.5) |
| TC (mmol/L)$^c$ | 4.70 | 3.83 | 5.26 | 4.66 | 3.63 | 4.42 (0.67) |
| HDL-C(mmol/L)$^d$ | 0.32 | 0.36 | 0.96 | 0.31 | 0.57 | 0.50 (0.28) |
| Non-HDL (mmol/L)$^e$ | 4.38 | 3.47 | 4.30 | 4.35 | 3.06 | 3.91 (0.61) |
| LDL-C (mmol/L)$^f$ | 3.36 | 2.59 | 3.32 | 2.69 | 2.25 | 2.85 (0.49) |
| VLDL-C (mmol/L)$^g$ | 0.88 | 0.88 | 0.98 | 1.66 | 0.80 | 1.04 (0.35) |
| Triglycerides (mmol/L)$^h$ | 2.20 | 1.55 | 1.14 | 4.35 | 1.38 | 2.12 (1.31) |

ASM = acid sphingomyelinase;
ASMD = acid sphingomyelinase deficiency;
C = cholesterol;
$DL_{co}$ = lung diffusion of carbon monoxide;
HDL = high-density lipoprotein;
LDL = low-density lipoprotein;
MN = mulitples of normal;
SD = standard deviation;
TC = total cholesterol;
VLDL = very low-density lipoprotein.
$^a$MN, multiples of normal calculated assuming normal spleen volume (L) is 0.2% body weight (kg), and normal liver volume (L) is 2.5% body weight (kg)
$^b$Normal $DL_{co}$ > 80%; Mildly reduced > 60% to ≤ 80%; Moderately reduced 40-60%; Severely reduced < 40%
$^c$Total cholesterol normal range; US < 5.18 mmol/L; UK 0-3.9 mmol/L
$^d$HDL normal range; US male > 0.777; US female > 0.9065 mmol/L; UK > 1.2 mmol/L
$^e$calculated as the difference between TC and HDL-C (Jacobsen et al. 2015)
$^f$LDL normal range: US < 3.3411 mmol/L; UK 0-2 mmol/L
$^g$VLDL normal range: US < 0.518 mmol/L; UK 0.09-0.71 mmol/L
$^h$Triglycerides normal range: <1.7 mmol/L Safety There were no deaths, serious or severe events, or discontinuations during 30 months of treatment. All patients had at least 1 AE, and almost all (826/838, 98.5%) were mild in intensity. Among 443 AEs considered related to treatment, 96 (21.7%) were considered IARs (including headache, nausea, abdominal pain, arthralgia, musculoskeletal pain and myalgia). Six moderate AEs considered IARs occurred during the Phase 1b study (first 6 months) and have been previously reported (Wasserstein et al. Mol. Genet. Metab. 116(1-2):88-97 (2015)). From 6-30 months in the LTS, 5 moderate AEs considered IARs included abdominal pain, hepatic pain, nausea, muscle spasm, and sensory disturbance in Patient 2. There were no hypersensitivity reactions, acute phase reactions, or cytokine release syndrome. No patient developed IgG antibodies to olipadase alfa. There were no clinically significant adverse changes in vital signs, hematology, or cardiac safety parameters.

Levels of inflammatory markers IL-6, IL-8, and hsCRP stable at the end of the Phase 1b study (Wasserstein et al. Mol. Genet. Metab. 116(1-2):88-97 (2015)) remained stable for all patients except Patient 2, who had fluctuations in hsCRP (1.10 to 33.3 mg/mL; normal range 0-5) from month 6 to month 30. Plasma ceramide levels for all patients (FIG. 1A) remained within normal limits (1.8-6.5 μg/mL).

Liver function enzyme levels remained within normal ranges for all patients until month 30 when Patient 4 had transient elevations in ALT (1.4× normal) and AST (2.9× normal), without corresponding AEs, and with subsequent normal levels. Total bilirubin and GGT levels remained similar to or below baseline levels for all patients. Iron levels fluctuated over time, but remained within or close to normal ranges.

During Phase 1b dose escalation, Patient 2 experienced IARs leading to repeat of the 2 mg/kg dose (Wasserstein et al. Mol. Genet. Metab. 116(1-2):88-97 (2015)). The patient subsequently received the target dose of 3 mg/kg through the Phase 1b trial and during the first 6 months of the LTS, at which time the patient reported mild AEs 7-10 days after most infusions including nausea, headache, fatigue, achiness, intermittent abdominal pain, and occasional fever (38.3 to 40.0° C.). Episodes lasted ~3 days and were completely resolved by the next infusion. Olipadase alfa was decreased (2 mg/kg for 6 months, then to the current dose of 1 mg/kg). Decreasing the dose did not change the timing, frequency, or types of events reported.

Efficacy

Spleen and Liver Volumes

Spleen and liver volumes decreased in all patients relative to baseline (FIG. 2A). Mean spleen volumes decreased from 12.8 multiples of normal (MN) at baseline to 6.7 MN at 30 months, a 47.3% decrease from baseline (p<0.0001). Mean liver volumes decreased from 1.7 MN at baseline to 1.07 MN at 30 months, a 35.6% decrease from baseline (p=0.006).

Infiltrative Lung Disease

Percent predicted DLco increased in all patients relative to baseline values (FIG. 2B) and improved from a mean of 53.2% (moderate) at baseline to 67.1% at 30 months (mild). The greatest changes occurred in the three patients with the lowest % predicted DLco values at baseline (<40%, in the severe range). FIG. 2B also shows assessment of infiltrative lung disease with mean scores for components at baseline, 6 months, 18 months, and 30 months. The data show progressive decreases in all parameters, particularly in GG appearance and RND, which almost completely resolved.

Fasting Lipid Parameters

Fasting lipid profiles are shown in FIGS. 4A-4D. By 30 months, triglycerides decreased by 42.99% (p=0.02), total cholesterol by 12.7% (p=0.04), LDL-C by 22.8% (p=0.007), and HDL-C increased by 137.6% (p=0.01). Non-HDL cholesterol level (total cholesterol minus HDL-C), was >3.37 mmol/L (>130 mg/dL) in 4/5 patients at baseline (mean 3.91 mmol/L) and was <3.37 mmol/L in all patients at 30 months (mean 2.66 mmol/L).

Biomarker Assessment

Figure 1B:
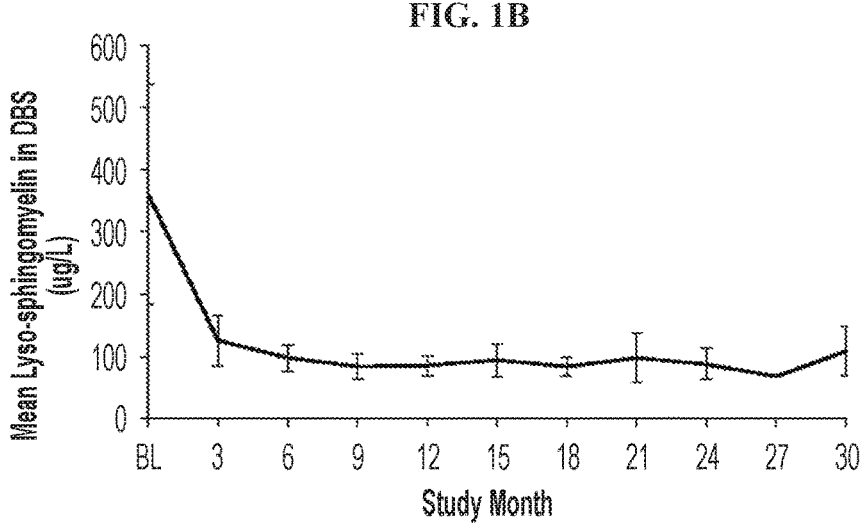

Mean lyso-sphingomyelin levels in DBS were 5 times above the upper limit of normal (ULN=69 µg/L) at baseline and decreased to near-normal levels that remained stable from 6 through 30 months (FIG. 1B).

Figure 1C:
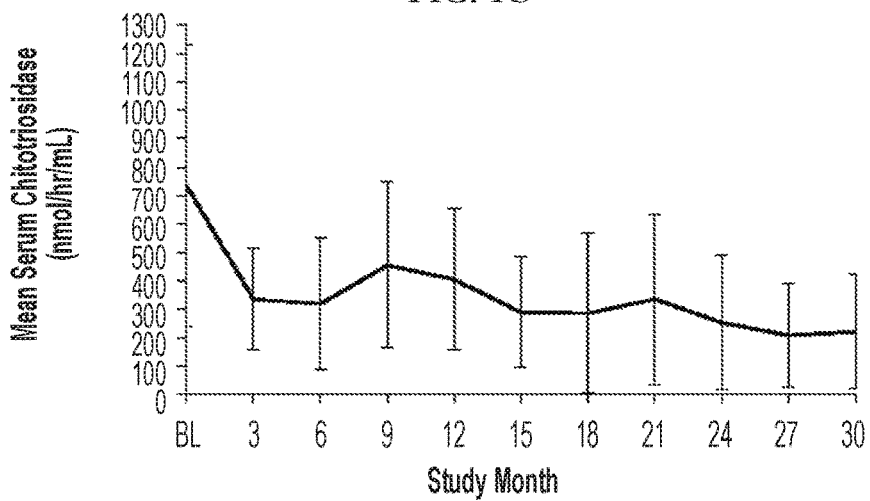

Pre-infusion serum chitotriosidase levels steadily decreased by 72.3% from 735 nmol/hr/mL at baseline to 221 nmol/hr/mL at 30 months (p=0.0007), approaching the upper limit of normal chitotriosidase range (<181 nmol/hr/mL) (FIG. 1C). Data were not adjusted to account for two patients heterozygous for a common 24-bp duplication which reduces serum chitotriosidase activity.

Hematology

Most patients maintained platelet counts just below normal or within the low-normal range. Patient 1 had values (57-102×109/L) below low-normal (150×109/L) throughout the study. Mean platelet count changes from baseline (increases) fluctuated over time [between 5.9% (month 27) and 25.7% (month 9)], and was 20.6% at 30 months. Hemoglobin levels remained similar to baseline levels (mean changes from baseline ranged from −6.1% at week 12 to 6.9% at month 24) and were within normal levels for all patients (data not shown).

Bone Density

At baseline, mean spinal T-scores were in the osteopenic range (between −1.0 and −2.5) at −1.48±1.14, while Z-scores indicated normal BMD (−1.36±1.26) within −1 standard deviation of the low BMD cutoff (−2.0). Both T- and Z-scores improved at 30 months (−0.94±1.03 and −0.78±1.11, respectively). Patient 2 (female, 32 year old at baseline) had a baseline spinal T-score (−3.06) in the osteoporotic range that improved at 18 (−2.48) and 30 months (−2.65) to values on the osteopenia/osteoporosis border. Two patients with T-scores in the osteopenic range at baseline (Patient 1, male 31 years old at baseline, −1.31 and Patient 4, male, 28 years old at baseline, −2.14) had scores in the normal range at 30 months (−0.76 and −0.82, respectively). Results for individual Z-scores over time were similar.

Mean femur T- and Z-scores were in the normal range at baseline (−0.38±1.35 and −0.27±1.46, respectively) and at 30 months (−0.28±1.27 and −0.13±1.4, respectively). Patient 2 had a baseline femur T-score in the osteopenic range (−2.23) and a Z-score indicating low BMD (−2.18); both improved slightly (−1.89 and −1.82, respectively) at 30 months.

Bone Marrow Burden

Figure 3B:
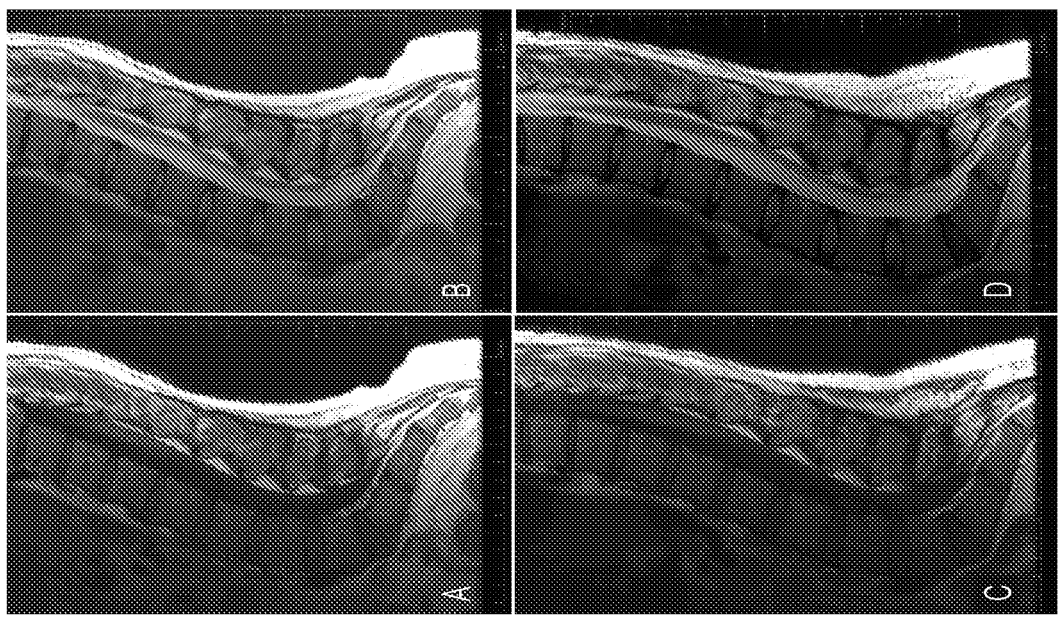
FIGS. 3A and 3B are photographs depicting the effect of olipudase alfa on bone marrow burden.
Figure 3A:
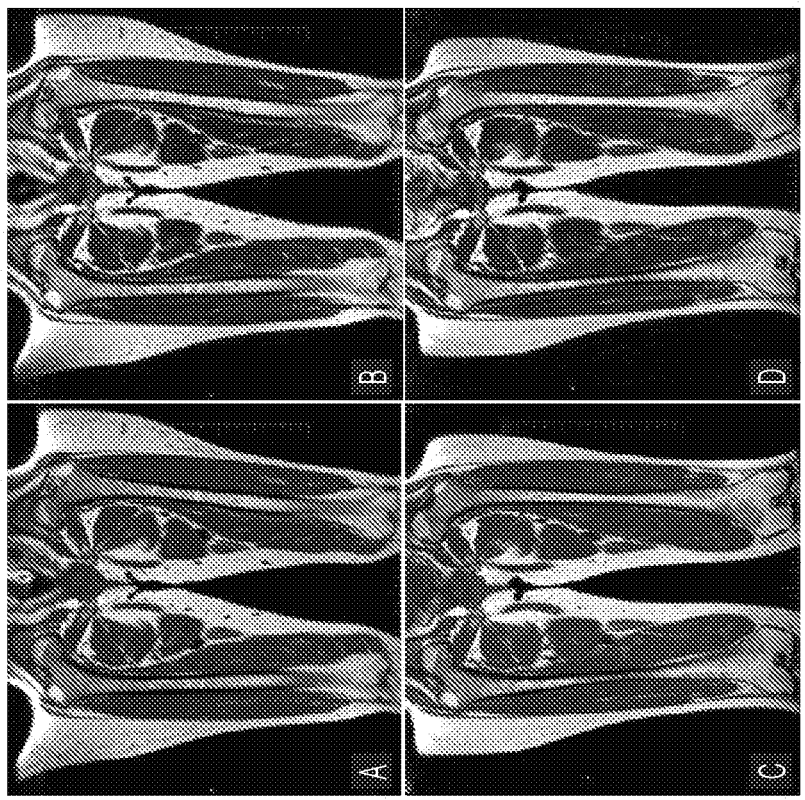

Mean categorical scores for BMB were similar at baseline (6.2±2.5) and 30 months (5.6±1.1). Patient 2 had the highest total BMB score of 10 at baseline, which improved by 3 points (score of 7) at 18 and 30 months. T1- and T2-weighted femur and spine images for Patient 2 at baseline and after 30 months of olipudase alfa treatment are shown in FIGS. 3A and 3B. Hypointensity of the proximal epiphysis bone marrow observed at baseline was reduced following 30 months of treatment. In spine, diffuse infiltration of the bone marrow and hyperintense signal intensity of presacral fat observed at baseline was unchanged and improved, respectively, after 30 months of treatment.

Patient Reported Outcomes

Mean BFI±SD fatigue scores were 3.04±2.29 at baseline and 2.44±3.44 at 30 months. Mean BPI±SD pain severity scores were 3.45±2.77 at baseline and 2.90±2.70 at 30 months, and mean BPI±SD pain interference scores were 2.03±1.58 at baseline and 3.29±3.51 at 30 months. Most of the individual BFI and BPI pain severity scores were in the mild (0-3) or moderate (4-6) categories at all time points. Exceptions were Patient 5, whose BPI pain was severe (7-10) at both baseline (6.8) and 30 months (7). BPI pain interference scores increased for Patients 2 (2 at baseline, 8.1 at 30 months) and 3 (1.9 at baseline, 5.3 at 30 months). Fatigue reported by Patient 2 was moderate (5.8) at baseline and severe (8.3) at 30 months.

This study demonstrates that treatment for 30 months with olipudase alfa, the first etiology-specific treatment in development for ASMD, is well-tolerated and associated with life-transforming sustained improvements in relevant disease clinical measures. The 30 months safety profile was similar to the Phase 1b study profile (Wasserstein et al., *Mol. Genet. Metab.* 116(1-2):88-97 (2015)). There were no hypersensitivity reactions and no anti-drug antibodies were detected. No cytokine release syndrome has been observed in any patient exposed to olipudase alfa to date. Since IARs were not immunologic reactions, they are likely related to release of biologically active sphingomyelin metabolites, principally ceramide, which is a signaling intermediary in cytokine release, inflammation, and apoptosis (Spiegel et al., *Curr. Opin. Cell Biol.* 8(2):159-167 (1996); Gulbins et al., *J. Mol. Med.* 82(6):357-363 (2004)). During the first six months of treatment, olipudase alfa doses elicited transient increases in plasma ceramide levels that generally peaked at 48 hour post-infusion (Wasserstein et al. *Mol. Genet. Metab.* 116(1-2):88-97 (2015)). Both pre- and post-infusion ceramide levels steadily decreased with each successive olipudase alfa infusion, plateauing after 3 months of treatment, and remaining stable through 30 months.

Clinical improvements were sustained throughout 30 months. Statistically significant improvements in liver and spleen volumes (mean percent decreases in liver volume of 31.2% and spleen of 39.3%) are comparable to responses of other lysosomal storage disorders to ERT. In Gaucher disease, the therapeutic goal for spleen volume is a 30% to 50% decrease during the first year of treatment, and for liver volume a 20% to 30% decrease within the first 2 years of treatment (Pastores et al., *Semin Hematol* 41 (Supple 5):4-14 (2004)).

Patients with chronic visceral or chronic neurovisceral ASMD demonstrate worsening of infiltrative lung disease with age (Wasserstein et al., *Pediatrics* 114(6):e672-677 (2004)). Over 30 months of treatment there was a 35% increase from baseline in lung diffusing capacity, with prominent changes in the 3 patients with the lowest DLCO at baseline. Improvements in lung disease scores observed during the first 6 months of treatment (Wasserstein et al. *Mol. Genet. Metab.* 116(1-2):88-97(2015)) continued during the subsequent 2 years of treatment, such that some parameters (e.g., GG appearance and RND) had normalized.

Atherogenic lipid profiles typically worsen with age in patients with chronic ASMD (Wasserstein et al., *Pediatrics* 114(6):e672-677(2004)), and lipid abnormalities may be associated with early coronary artery disease (McGovern et al., *J. Pediatr.* 145(1):77-81(2004)). At baseline, patients were at mild-to-moderate risk for cardiovascular disease based on lipid profiles (Wasserstein et al. *Mol. Genet. Metab.* 116(1-2):88-97(2015)), and profiles improved over 30 months of treatment. Non-HDL cholesterol level is considered a good predictor of cardiovascular risk in many patient populations, and a desirable level is <3.37 mmol/L (<130 mg/dL) (Jacobson et al., *J. Clin. Lipidol.* 9(2):129-169 (2015)). All but one patient had non-HDL levels above 3.37 mmol/L before ERT, and at 30 months total cholesterol and HDL levels improved for all patients with non-HDL below the 3.37 mmol/L cutoff.

Skeletal complications are also prominent features of chronic ASMD. Improvements in BMD were noted in some patients, particularly in the spine, demonstrating that olipudase alfa has a beneficial effect on BMD in adults with ASMD. In other lipid storage disorders with low BMD such as Gaucher disease, ERT in combination with antiresorptive therapy can improve osteopenia (Wenstrup et al., *Blood* 104(5):1253-1257 (2004)), although response of bone disease to ERT alone is slow in adult patients (Wenstrup et al *J. Bone Miner. Res.* 22(1):119-126 (2007)). However, bisphosphonates may not be appropriate in patients with ASMD due to inhibition of ASM activity (Arenz *Cell Physiol. Biochem.* 26(1):1-8 (2010)). No study patient was receiving bisphosphonate therapy. Results from this study indicate that osteopenia will be improved with olipudase alfa alone.

Other clinical measures showed improvements or stability during ERT. Platelet counts and hemoglobin levels remained stable. Moderate levels of BMB were measured at baseline and after 30 months of olipudase alfa treatment, with improvements noted in some patients. Patients had mild to moderate levels of pain and fatigue at baseline that remained stable at 30 months for most patients. Worsening of patient reported outcomes for Patient 3 was not associated with AEs. Patient 2 reported worsening of fatigue and pain with AEs characterized by flu-like symptoms after one year of ERT. This patient has atypical lupus erythematosus and it is uncertain whether this contributed to fatigue and pain, AEs and inflammatory cytokine fluctuations. Decreasing olipudase alfa to 1 mg/kg/week in this patient has had no impact on AE incidence, fatigue or pain. At the lower olipudase alfa dose (12 months of exposure), the patient continues to have clinical benefit including reduced spleen and liver volumes as well as improvement in percent predicted DLco, sustained clearance of infiltrative HRCT parameters, and stabilization of biomarkers.

Chitotriosidase, a well-known biomarker for therapeutic monitoring during ERT in Gaucher disease (Guo et al., *J. Inherit. Metab. Dis.* 18(6):717-722 (1995)), and a marker of chronic inflammatory diseases, steadily decreased during olipudase alfa treatment (Boot et al., *Clin Chim Acta* 411 (1-2):31-36 (2010)). Lyso-sphingomyelin, the deacylated form of sphingomyelin, decreased in DBS, suggesting utility as a biomarker for monitoring ERT outcomes reflected by steady decreases as patients undergo debulking of sphingomyelin, followed by stability during long-term treatment. Lyso-sphingomyelin is elevated approximately 5-fold in DBS from patients with chronic visceral ASMD (Chuang *Mol. Genet. Metab.* 111(2):209-211 (2014)).

This open-label extension study of olipudase alfa demonstrates that treatment with olipudase alfa for 30 months was well-tolerated and clinically effective.

What is claimed is:

1. A method of treating an abnormal bone condition in a patient with acid sphingomyelinase deficiency (ASMD), comprising:
 selecting a patient with ASMD for treatment of an abnormal bone condition,
 administering to the patient a plurality of doses of recombinant human acid sphingomyelinase (rhASM) over a period of six to thirty months,
 measuring a bone indicator of the patient, and
 comparing the bone indicator of the patient to the baseline bone indicator of the patient before the administering step, wherein the patient's bone indicator improves after the plurality of doses of rhASM.

2. The method of claim 1, wherein the bone indicator is
 (i) bone mineral density (BMD), wherein the BMD improves after the plurality of doses of rhASM,
 (ii) bone marrow burden (BMB), wherein the BMB decreases after the plurality of doses of rhASM,
 (iii) bone maturation, wherein the bone maturation improves after the plurality of doses of rhASM, or
 (iv) linear growth, wherein the linear growth improves after the plurality of doses of rhASM.

3. The method of claim 1, wherein the abnormal bone condition is osteopenia or osteoporosis.

4. The method of claim 1, wherein the patient has Niemann-Pick disease type B.

5. The method of claim 1, wherein the patient has Niemann-Pick disease type A/B.

6. The method of claim 1, wherein the patient is an adult patient.

7. The method of claim 1, wherein the patient is a pediatric patient.

8. The method of claim 1, wherein
 (i) the first two or more doses are escalating doses and are administered at a successively increasing amount,
 (ii) the doses after the escalating doses are maintenance doses and are administered in the same amount as or less than the last escalating dose,
 (iii) the first dose is in the amount of 0.1 mg/kg and the patient is a pediatric patient,
 (iv) the first dose is in the amount of 0.1 mg/kg and the patient is an adult patient,
 (v) the highest maintenance dose is in the amount of 0.3 mg/kg to 3 mg/kg,
 (vi) the highest maintenance dose is in the amount of 1 mg/kg,
 (vii) the highest maintenance dose is in the amount of 2 mg/kg,
 (viii) the highest maintenance dose is in the amount of 3 mg/kg,
 (ix) the highest maintenance dose is the highest dose tolerated by the patient, and/or
 (x) the escalating doses are administered in the order of 0.1 mg/kg, 0.3 mg/kg, 0.3 mg/kg, 0.6 mg/kg, 0.6 mg/kg, 1.0 mg/kg, 2.0 mg/kg, and 3.0 mg/kg.

9. The method of claim 1, wherein the plurality of doses are administered at an interval of every 2 weeks.

10. The method of claim 1, wherein the plurality of doses are administered through intravenous injection.

11. The method of claim 1, wherein the rhASM is olipudase alfa.

* * * * *

SEQUENCE LISTING

```
<160> NUMBER OF SEQ ID NOS: 4

<210> SEQ ID NO 1
<211> LENGTH: 627
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Met Ala Arg Tyr Gly Ala Ser Leu Arg Gln Ser Cys Pro Arg Ser Gly
1               5                   10                  15

Arg Glu Gln Gly Gln Asp Gly Thr Ala Gly Ala Pro Gly Leu Leu Trp
            20                  25                  30

Met Gly Leu Ala Leu Ala Leu Ala Leu Ala Leu Ala Leu Ser Asp Ser
        35                  40                  45

Arg Val Leu Trp Ala Pro Ala Glu Ala His Pro Leu Ser Pro Gln Gly
    50                  55                  60

His Pro Ala Arg Leu His Arg Ile Val Pro Arg Leu Arg Asp Val Phe
65                  70                  75                  80

Gly Trp Gly Asn Leu Thr Cys Pro Ile Cys Lys Gly Leu Phe Thr Ala
                85                  90                  95

Ile Asn Leu Gly Leu Lys Lys Glu Pro Asn Val Ala Arg Val Gly Ser
            100                 105                 110

Val Ala Ile Lys Leu Cys Asn Leu Leu Lys Ile Ala Pro Pro Ala Val
        115                 120                 125
```

```
Cys Gln Ser Ile Val His Leu Phe Glu Asp Asp Met Val Glu Val Trp
    130                 135                 140
Arg Arg Ser Val Leu Ser Pro Ser Glu Ala Cys Gly Leu Leu Leu Gly
145                 150                 155                 160
Ser Thr Cys Gly His Trp Asp Ile Phe Ser Ser Trp Asn Ile Ser Leu
                165                 170                 175
Pro Thr Val Pro Lys Pro Pro Lys Pro Ser Pro Pro Ala Pro
                180                 185                 190
Gly Ala Pro Val Ser Arg Ile Leu Phe Leu Thr Asp Leu His Trp Asp
        195                 200                 205
His Asp Tyr Leu Glu Gly Thr Asp Pro Asp Cys Ala Asp Pro Leu Cys
    210                 215                 220
Cys Arg Arg Gly Ser Gly Leu Pro Pro Ala Ser Arg Pro Gly Ala Gly
225                 230                 235                 240
Tyr Trp Gly Glu Tyr Ser Lys Cys Asp Leu Pro Leu Arg Thr Leu Glu
                245                 250                 255
Ser Leu Leu Ser Gly Leu Gly Pro Ala Gly Pro Phe Asp Met Val Tyr
                260                 265                 270
Trp Thr Gly Asp Ile Pro Ala His Asp Val Trp His Gln Thr Arg Gln
                275                 280                 285
Asp Gln Leu Arg Ala Leu Thr Thr Val Thr Ala Leu Val Arg Lys Phe
    290                 295                 300
Leu Gly Pro Val Pro Val Tyr Pro Ala Val Gly Asn His Glu Ser Thr
305                 310                 315                 320
Pro Val Asn Ser Phe Pro Pro Pro Phe Ile Glu Gly Asn His Ser Ser
                325                 330                 335
Arg Trp Leu Tyr Glu Ala Met Ala Lys Ala Trp Glu Pro Trp Leu Pro
                340                 345                 350
Ala Glu Ala Leu Arg Thr Leu Arg Ile Gly Gly Phe Tyr Ala Leu Ser
                355                 360                 365
Pro Tyr Pro Gly Leu Arg Leu Ile Ser Leu Asn Met Asn Phe Cys Ser
    370                 375                 380
Arg Glu Asn Phe Trp Leu Leu Ile Asn Ser Thr Asp Pro Ala Gly Gln
385                 390                 395                 400
Leu Gln Trp Leu Val Gly Glu Leu Gln Ala Ala Glu Asp Arg Gly Asp
                405                 410                 415
Lys Val His Ile Ile Gly His Ile Pro Pro Gly His Cys Leu Lys Ser
                420                 425                 430
Trp Ser Trp Asn Tyr Tyr Arg Ile Val Ala Arg Tyr Glu Asn Thr Leu
                435                 440                 445
Ala Ala Gln Phe Phe Gly His Thr His Val Asp Glu Phe Glu Val Phe
    450                 455                 460
Tyr Asp Glu Glu Thr Leu Ser Arg Pro Leu Ala Val Ala Phe Leu Ala
465                 470                 475                 480
Pro Ser Ala Thr Thr Tyr Ile Gly Leu Asn Pro Gly Tyr Arg Val Tyr
                485                 490                 495
Gln Ile Asp Gly Asn Tyr Ser Gly Ser Ser His Val Val Leu Asp His
                500                 505                 510
Glu Thr Tyr Ile Leu Asn Leu Thr Gln Ala Asn Ile Pro Gly Ala Ile
        515                 520                 525
Pro His Trp Gln Leu Leu Tyr Arg Ala Arg Glu Thr Tyr Gly Leu Pro
    530                 535                 540
```

```
Asn Thr Leu Pro Thr Ala Trp His Asn Leu Val Tyr Arg Met Arg Gly
545                 550                 555                 560

Asp Met Gln Leu Phe Gln Thr Phe Trp Phe Leu Tyr His Lys Gly His
                565                 570                 575

Pro Pro Ser Glu Pro Cys Gly Thr Pro Cys Arg Leu Ala Thr Leu Cys
            580                 585                 590

Ala Gln Leu Ser Ala Arg Ala Asp Ser Pro Ala Leu Cys Arg His Leu
        595                 600                 605

Met Pro Asp Gly Ser Leu Pro Glu Ala Gln Ser Leu Trp Pro Arg Pro
610                 615                 620

Leu Phe Cys
625

<210> SEQ ID NO 2
<211> LENGTH: 570
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

His Pro Leu Ser Pro Gln Gly His Pro Ala Arg Leu His Arg Ile Val
1               5                   10                  15

Pro Arg Leu Arg Asp Val Phe Gly Trp Gly Asn Leu Thr Cys Pro Ile
                20                  25                  30

Cys Lys Gly Leu Phe Thr Ala Ile Asn Leu Gly Leu Lys Lys Glu Pro
            35                  40                  45

Asn Val Ala Arg Val Gly Ser Val Ala Ile Lys Leu Cys Asn Leu Leu
        50                  55                  60

Lys Ile Ala Pro Pro Ala Val Cys Gln Ser Ile Val His Leu Phe Glu
65                  70                  75                  80

Asp Asp Met Val Glu Val Trp Arg Arg Ser Val Leu Ser Pro Ser Glu
                85                  90                  95

Ala Cys Gly Leu Leu Leu Gly Ser Thr Cys Gly His Trp Asp Ile Phe
            100                 105                 110

Ser Ser Trp Asn Ile Ser Leu Pro Thr Val Pro Lys Pro Pro Pro Lys
        115                 120                 125

Pro Pro Ser Pro Pro Ala Pro Gly Ala Pro Val Ser Arg Ile Leu Phe
    130                 135                 140

Leu Thr Asp Leu His Trp Asp His Asp Tyr Leu Glu Gly Thr Asp Pro
145                 150                 155                 160

Asp Cys Ala Asp Pro Leu Cys Cys Arg Arg Gly Ser Gly Leu Pro Pro
                165                 170                 175

Ala Ser Arg Pro Gly Ala Gly Tyr Trp Gly Glu Tyr Ser Lys Cys Asp
            180                 185                 190

Leu Pro Leu Arg Thr Leu Glu Ser Leu Leu Ser Gly Leu Gly Pro Ala
        195                 200                 205

Gly Pro Phe Asp Met Val Tyr Trp Thr Gly Asp Ile Pro Ala His Asp
    210                 215                 220

Val Trp His Gln Thr Arg Gln Asp Gln Leu Arg Ala Leu Thr Thr Val
225                 230                 235                 240

Thr Ala Leu Val Arg Lys Phe Leu Gly Pro Val Pro Val Tyr Pro Ala
                245                 250                 255
```

Val Gly Asn His Glu Ser Thr Pro Val Asn Ser Phe Pro Pro Phe
            260                 265                 270

Ile Glu Gly Asn His Ser Ser Arg Trp Leu Tyr Glu Ala Met Ala Lys
            275                 280                 285

Ala Trp Glu Pro Trp Leu Pro Ala Glu Ala Leu Arg Thr Leu Arg Ile
290                 295                 300

Gly Gly Phe Tyr Ala Leu Ser Pro Tyr Pro Gly Leu Arg Leu Ile Ser
305                 310                 315                 320

Leu Asn Met Asn Phe Cys Ser Arg Glu Asn Phe Trp Leu Leu Ile Asn
            325                 330                 335

Ser Thr Asp Pro Ala Gly Gln Leu Gln Trp Leu Val Gly Glu Leu Gln
            340                 345                 350

Ala Ala Glu Asp Arg Gly Asp Lys Val His Ile Ile Gly His Ile Pro
            355                 360                 365

Pro Gly His Cys Leu Lys Ser Trp Ser Trp Asn Tyr Tyr Arg Ile Val
            370                 375                 380

Ala Arg Tyr Glu Asn Thr Leu Ala Ala Gln Phe Phe Gly His Thr His
385                 390                 395                 400

Val Asp Glu Phe Glu Val Phe Tyr Asp Glu Glu Thr Leu Ser Arg Pro
            405                 410                 415

Leu Ala Val Ala Phe Leu Ala Pro Ser Ala Thr Thr Tyr Ile Gly Leu
            420                 425                 430

Asn Pro Gly Tyr Arg Val Tyr Gln Ile Asp Gly Asn Tyr Ser Gly Ser
            435                 440                 445

Ser His Val Val Leu Asp His Glu Thr Tyr Ile Leu Asn Leu Thr Gln
            450                 455                 460

Ala Asn Ile Pro Gly Ala Ile Pro His Trp Gln Leu Leu Tyr Arg Ala
465                 470                 475                 480

Arg Glu Thr Tyr Gly Leu Pro Asn Thr Leu Pro Thr Ala Trp His Asn
            485                 490                 495

Leu Val Tyr Arg Met Arg Gly Asp Met Gln Leu Phe Gln Thr Phe Trp
            500                 505                 510

Phe Leu Tyr His Lys Gly His Pro Pro Ser Glu Pro Cys Gly Thr Pro
            515                 520                 525

Cys Arg Leu Ala Thr Leu Cys Ala Gln Leu Ser Ala Arg Ala Asp Ser
            530                 535                 540

Pro Ala Leu Cys Arg His Leu Met Pro Asp Gly Ser Leu Pro Glu Ala
545                 550                 555                 560

Gln Ser Leu Trp Pro Arg Pro Leu Phe Cys
            565                 570

<210> SEQ ID NO 3
<211> LENGTH: 629
<212> TYPE: PRT
<213> ORGANISM: Homo sapiens

<400> SEQUENCE: 3

Met Pro Arg Tyr Gly Ala Ser Leu Arg Gln Ser Cys Pro Arg Ser Gly
1               5                   10                  15

Arg Glu Gln Gly Gln Asp Gly Thr Ala Gly Ala Pro Gly Leu Leu Trp
            20                  25                  30

Met Gly Leu Val Leu Ala Leu Ala Leu Ala Leu Ala Leu Ser
            35                  40                  45

```
Asp Ser Arg Val Leu Trp Ala Pro Ala Glu Ala His Pro Leu Ser Pro
 50                  55                  60

Gln Gly His Pro Ala Arg Leu His Arg Ile Val Pro Arg Leu Arg Asp
 65                  70                  75                  80

Val Phe Gly Trp Gly Asn Leu Thr Cys Pro Ile Cys Lys Gly Leu Phe
                 85                  90                  95

Thr Ala Ile Asn Leu Gly Leu Lys Lys Glu Pro Asn Val Ala Arg Val
            100                 105                 110

Gly Ser Val Ala Ile Lys Leu Cys Asn Leu Leu Lys Ile Ala Pro Pro
        115                 120                 125

Ala Val Cys Gln Ser Ile Val His Leu Phe Glu Asp Asp Met Val Glu
130                 135                 140

Val Trp Arg Arg Ser Val Leu Ser Pro Ser Glu Ala Cys Gly Leu Leu
145                 150                 155                 160

Leu Gly Ser Thr Cys Gly His Trp Asp Ile Phe Ser Ser Trp Asn Ile
                165                 170                 175

Ser Leu Pro Thr Val Pro Lys Pro Pro Lys Pro Ser Pro Pro
            180                 185                 190

Ala Pro Gly Ala Pro Val Ser Arg Ile Leu Phe Leu Thr Asp Leu His
        195                 200                 205

Trp Asp His Asp Tyr Leu Glu Gly Thr Asp Pro Asp Cys Ala Asp Pro
210                 215                 220

Leu Cys Cys Arg Arg Gly Ser Gly Leu Pro Pro Ala Ser Arg Pro Gly
225                 230                 235                 240

Ala Gly Tyr Trp Gly Glu Tyr Ser Lys Cys Asp Leu Pro Leu Arg Thr
                245                 250                 255

Leu Glu Ser Leu Leu Ser Gly Leu Gly Pro Ala Gly Pro Phe Asp Met
            260                 265                 270

Val Tyr Trp Thr Gly Asp Ile Pro Ala His Asp Val Trp His Gln Thr
        275                 280                 285

Arg Gln Asp Gln Leu Arg Ala Leu Thr Thr Val Thr Ala Leu Val Arg
290                 295                 300

Lys Phe Leu Gly Pro Val Pro Val Tyr Pro Ala Val Gly Asn His Glu
305                 310                 315                 320

Ser Ile Pro Val Asn Ser Phe Pro Pro Pro Phe Ile Glu Gly Asn His
                325                 330                 335

Ser Ser Arg Trp Leu Tyr Glu Ala Met Ala Lys Ala Trp Glu Pro Trp
            340                 345                 350

Leu Pro Ala Glu Ala Leu Arg Thr Leu Arg Ile Gly Gly Phe Tyr Ala
        355                 360                 365

Leu Ser Pro Tyr Pro Gly Leu Arg Leu Ile Ser Leu Asn Met Asn Phe
370                 375                 380

Cys Ser Arg Glu Asn Phe Trp Leu Leu Ile Asn Ser Thr Asp Pro Ala
385                 390                 395                 400

Gly Gln Leu Gln Trp Leu Val Gly Glu Leu Gln Ala Ala Glu Asp Arg
                405                 410                 415

Gly Asp Lys Val His Ile Ile Gly His Ile Pro Pro Gly His Cys Leu
            420                 425                 430

Lys Ser Trp Ser Trp Asn Tyr Tyr Arg Ile Val Ala Arg Tyr Glu Asn
        435                 440                 445

Thr Leu Ala Ala Gln Phe Phe Gly His Thr His Val Asp Glu Phe Glu
450                 455                 460
```

-continued

```
Val Phe Tyr Asp Glu Glu Thr Leu Ser Arg Pro Leu Ala Val Ala Phe
465                 470                 475                 480

Leu Ala Pro Ser Ala Thr Thr Tyr Ile Gly Leu Asn Pro Gly Tyr Arg
            485                 490                 495

Val Tyr Gln Ile Asp Gly Asn Tyr Ser Arg Ser Ser His Val Val Leu
        500                 505                 510

Asp His Glu Thr Tyr Ile Leu Asn Leu Thr Gln Ala Asn Ile Pro Gly
    515                 520                 525

Ala Ile Pro His Trp Gln Leu Leu Tyr Arg Ala Arg Glu Thr Tyr Gly
530                 535                 540

Leu Pro Asn Thr Leu Pro Thr Ala Trp His Asn Leu Val Tyr Arg Met
545                 550                 555                 560

Arg Gly Asp Met Gln Leu Phe Gln Thr Phe Trp Phe Leu Tyr His Lys
            565                 570                 575

Gly His Pro Pro Ser Glu Pro Cys Gly Thr Pro Cys Arg Leu Ala Thr
        580                 585                 590

Leu Cys Ala Gln Leu Ser Ala Arg Ala Asp Ser Pro Ala Leu Cys Arg
    595                 600                 605

His Leu Met Pro Asp Gly Ser Leu Pro Glu Ala Gln Ser Leu Trp Pro
610                 615                 620

Arg Pro Leu Phe Cys
625

<210> SEQ ID NO 4
<211> LENGTH: 629
<212> TYPE: PRT
<213> ORGANISM: Homo sapiens

<400> SEQUENCE: 4

Met Pro Arg Tyr Gly Ala Ser Leu Arg Gln Ser Cys Pro Arg Ser Gly
1               5                   10                  15

Arg Glu Gln Gly Gln Asp Gly Thr Ala Gly Ala Pro Gly Leu Leu Trp
            20                  25                  30

Met Gly Leu Val Leu Ala Leu Ala Leu Ala Leu Ala Leu Ala Leu Ser
        35                  40                  45

Asp Ser Arg Val Leu Trp Ala Pro Ala Glu Ala His Pro Leu Ser Pro
50                  55                  60

Gln Gly His Pro Ala Arg Leu His Arg Ile Val Pro Arg Leu Arg Asp
65                  70                  75                  80

Val Phe Gly Trp Gly Asn Leu Thr Cys Pro Ile Cys Lys Gly Leu Phe
            85                  90                  95

Thr Ala Ile Asn Leu Gly Leu Lys Lys Glu Pro Asn Val Ala Arg Val
        100                 105                 110

Gly Ser Val Ala Ile Lys Leu Cys Asn Leu Leu Lys Ile Ala Pro Pro
    115                 120                 125

Ala Val Cys Gln Ser Ile Val His Leu Phe Glu Asp Asp Met Val Glu
130                 135                 140

Val Trp Arg Arg Ser Val Leu Ser Pro Ser Glu Ala Cys Gly Leu Leu
145                 150                 155                 160

Leu Gly Ser Thr Cys Gly His Trp Asp Ile Phe Ser Ser Trp Asn Ile
            165                 170                 175

Ser Leu Pro Thr Val Pro Lys Pro Pro Lys Pro Ser Pro Pro
        180                 185                 190

Ala Pro Gly Ala Pro Val Ser Arg Ile Leu Phe Leu Thr Asp Leu His
    195                 200                 205
```

-continued

Trp Asp His Asp Tyr Leu Glu Gly Thr Asp Pro Asp Cys Ala Asp Pro
210                215                220

Leu Cys Cys Arg Arg Gly Ser Gly Leu Pro Pro Ala Ser Arg Pro Gly
225                230                235                240

Ala Gly Tyr Trp Gly Glu Tyr Ser Lys Cys Asp Leu Pro Leu Arg Thr
            245                250                255

Leu Glu Ser Leu Leu Ser Gly Leu Gly Pro Ala Gly Pro Phe Asp Met
        260                265                270

Val Tyr Trp Thr Gly Asp Ile Pro Ala His Asp Val Trp His Gln Thr
    275                280                285

Arg Gln Asp Gln Leu Arg Ala Leu Thr Thr Val Thr Ala Leu Val Arg
290                295                300

Lys Phe Leu Gly Pro Val Pro Val Tyr Pro Ala Val Gly Asn His Glu
305                310                315                320

Ser Thr Pro Val Asn Ser Phe Pro Pro Phe Ile Glu Gly Asn His
            325                330                335

Ser Ser Arg Trp Leu Tyr Glu Ala Met Ala Lys Ala Trp Glu Pro Trp
            340                345                350

Leu Pro Ala Glu Ala Leu Arg Thr Leu Arg Ile Gly Gly Phe Tyr Ala
        355                360                365

Leu Ser Pro Tyr Pro Gly Leu Arg Leu Ile Ser Leu Asn Met Asn Phe
    370                375                380

Cys Ser Arg Glu Asn Phe Trp Leu Leu Ile Asn Ser Thr Asp Pro Ala
385                390                395                400

Gly Gln Leu Gln Trp Leu Val Gly Glu Leu Gln Ala Ala Glu Asp Arg
            405                410                415

Gly Asp Lys Val His Ile Ile Gly His Ile Pro Pro Gly His Cys Leu
            420                425                430

Lys Ser Trp Ser Trp Asn Tyr Tyr Arg Ile Val Ala Arg Tyr Glu Asn
            435                440                445

Thr Leu Ala Ala Gln Phe Phe Gly His Thr His Val Asp Glu Phe Glu
    450                455                460

Val Phe Tyr Asp Glu Glu Thr Leu Ser Arg Pro Leu Ala Val Ala Phe
465                470                475                480

Leu Ala Pro Ser Ala Thr Thr Tyr Ile Gly Leu Asn Pro Gly Tyr Arg
            485                490                495

Val Tyr Gln Ile Asp Gly Asn Tyr Ser Gly Ser Ser His Val Val Leu
            500                505                510

Asp His Glu Thr Tyr Ile Leu Asn Leu Thr Gln Ala Asn Ile Pro Gly
    515                520                525

Ala Ile Pro His Trp Gln Leu Leu Tyr Arg Ala Arg Glu Thr Tyr Gly
        530                535                540

Leu Pro Asn Thr Leu Pro Thr Ala Trp His Asn Leu Val Tyr Arg Met
545                550                555                560

Arg Gly Asp Met Gln Leu Phe Gln Thr Phe Trp Phe Leu Tyr His Lys
            565                570                575

Gly His Pro Pro Ser Glu Pro Cys Gly Thr Pro Cys Arg Leu Ala Thr
            580                585                590

Leu Cys Ala Gln Leu Ser Ala Arg Ala Asp Ser Pro Ala Leu Cys Arg
            595                600                605

```
His Leu Met Pro Asp Gly Ser Leu Pro Glu Ala Gln Ser Leu Trp Pro
    610                 615                 620
Arg Pro Leu Phe Cys
625
```